US006849658B2

(12) United States Patent
Bernardon et al.

(10) Patent No.: US 6,849,658 B2
(45) Date of Patent: *Feb. 1, 2005

(54) BIAROMATIC COMPOUNDS AND PHARMACEUTICAL AND COSMETIC COMPOSITIONS COMPRISING THEM

(75) Inventors: Jean-Michel Bernardon, Le Rouret (FR); Simon Trouille, Le Rouret (FR)

(73) Assignee: Galderma Research & Development, Valbonne (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/984,830

(22) Filed: Oct. 31, 2001

(65) Prior Publication Data

US 2003/0216586 A1 Nov. 20, 2003

Related U.S. Application Data

(62) Division of application No. 09/577,345, filed on May 25, 2000, which is a division of application No. 09/242,130, filed as application No. PCT/FR98/01238 on Jun. 12, 1998, now Pat. No. 6,103,762.

(30) Foreign Application Priority Data

Jun. 13, 1997 (FR) ............................................. 97 07358

(51) Int. Cl.[7] ...................... A61K 31/37; A61K 31/381; A61K 31/382; C07D 335/04; C07D 319/16

(52) U.S. Cl. ...................... 514/432; 514/438; 514/456; 514/457; 549/13; 549/49; 549/398; 544/145; 544/147; 546/202

(58) Field of Search ............................ 549/13, 49, 398; 514/432, 438, 456, 457; 544/145, 147; 546/202

(56) References Cited

U.S. PATENT DOCUMENTS

| | | | |
|---|---|---|---|
| 5,468,879 A | | 11/1995 | Chandraratna |
| 5,677,451 A | | 10/1997 | Chandraratna |
| 5,716,624 A | * | 2/1998 | Bernardon .................. 424/401 |
| 6,046,220 A | * | 4/2000 | Bernardon .................. 424/401 |
| 6,103,762 A | | 8/2000 | Bernardon et al. |
| 6,162,445 A | * | 12/2000 | Bernardon .................. 424/401 |
| 6,313,162 B1 | * | 11/2001 | Bernardon .................. 514/432 |
| 6,368,608 B1 | * | 4/2002 | Bernardon .................. 424/401 |

FOREIGN PATENT DOCUMENTS

| | | | |
|---|---|---|---|
| EP | 0661258 | * | 5/1995 |
| EP | 0 661 258 | | 7/1995 |
| WO | WO 93 16068 A | | 8/1993 |
| WO | WO 93 16083 A | | 9/1993 |
| WO | WO 96 11902 A | | 4/1996 |

OTHER PUBLICATIONS

Siegrist Adolf et al., Caplus 83:147317, Abstract DE 2453357, May 22, 1975.
Hiroyuki Kagechika et al., "Retinobenzoic Acids 2", Journal of Medicinal Chemistry, vol. 32, 1989, pp. 834–840, XP000569639 Washington US see p. 834; figure 1, table II.
Abhijit Bhat et al, Tetrahedron Letters, Jan. 1999. vol. 40, Novel Synthetic Routes . . . .
Kundu et al., J. Chem. Research (S) 1995, 4–5.

* cited by examiner

*Primary Examiner*—Rita Desai
(74) *Attorney, Agent, or Firm*—Nixon & Vanderhye P.C.

(57) ABSTRACT

The invention concerns bi-aromatic compounds of formula (I) in which Ar represents (a), Z being O or S, $R_1$ is $CH_3$, $-CH_2-O-R_6$, $-OR_6$ or $-COR_7$; $R_2$ is $-OR_8$, $-SR_8$ or a polyether radical if in the latter case $R_4$ is $C_1-C_{20}$alkyl and is in ortho or meta position relative to X—Ar; $R_3$ is alkyl or $R_2$ and $R_3$ together form a cycle optionally interrupted by O or S; $R_4$ is aryl radical; $R_5$ is H, halogen, $C_1-C_{20}$ alkyl or $-OR_8$; $R_6$ is H, alkyl or $-COR_9$; $R_7$ is H, alkyl, $-N(r')(r'')$ or $-OR_{10}$; $R_8$ is H, alkyl or $-COR_9$; $R_9$ is alkyl; $R_{10}$ is H, $C_1-C_{20}$ alkyl, alkenyl, monohydroxyalkyl or polyhydroxyalkyl, aryl or aralkyl or a sugar residue, r' and r" are H, alkyl mono- or polyhydroxyalkyl, aryl, an amino acid or sugar residue or together form a heterocycle, X represents a radical of formula (d) or (e) in which $R_{11}$ is H or $-OR_6$; $R_{12}$ is H or alkyl; or $R_{11}$ and $R_{12}$ form an oxo radical, and the salts, optical and geometrical isomers of the compounds of formula (I).

29 Claims, No Drawings

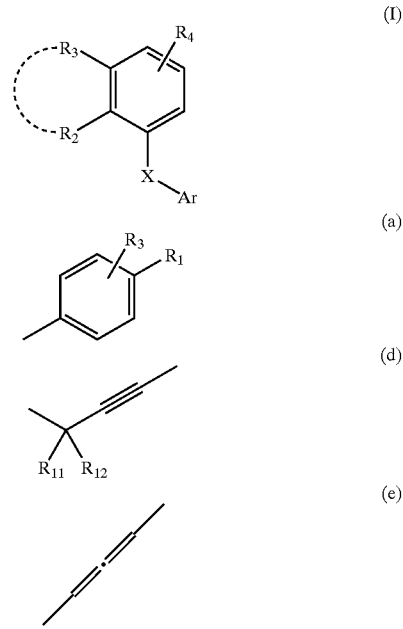

BIAROMATIC COMPOUNDS AND PHARMACEUTICAL AND COSMETIC COMPOSITIONS COMPRISING THEM

This is a divisional of application Ser. No. 09/577,345, filed May 25, 2000, allowed, which is a divisional of application Ser. No. 09/242,130, filed Mar. 23, 1999, now U.S. Pat. No. 6,103,762, which is a 371 application of PCT/FR98/01238, filed Jun. 12, 1998, the entire contents of which is hereby incorporated by reference in this application.

The invention relates, as novel and useful industrial products, to biaromatic compounds in which the aromatic nuclei are connected by a propynylene or allenylene divalent radical. It also relates to the use of these novel compounds in pharmaceutical compositions intended for use in human or veterinary medicine or alternatively in cosmetic compositions.

The compounds according to the invention have a marked activity in the fields of cell differentiation and proliferation, and they find applications more particularly in the topical and systemic treatment of dermatological conditions linked to a keratinization disorder, dermatological conditions (and the like) with an inflammatory and/or immunoallergic component, and dermal or epidermal proliferation, whether benign or malignant. These compounds can, in addition, be used in the treatment of degenerative diseases of the connective tissue, for combating skin ageing, whether photoinduced or chronologic, and treating cicatrization disorders. Furthermore, they find an application in the ophthalmological field, in particular in the treatment of corneopathies.

It is also possible to use the compounds according to the invention in cosmetic compositions for body and hair hygiene.

EP-061,258 has already disclosed biaromatic compounds, the aromatic nuclei of which are connected by a propynylene divalent radical, as substances which are active in pharmaceutical or cosmetic compositions.

The compounds according to EP-661,258 correspond to the following general formula:

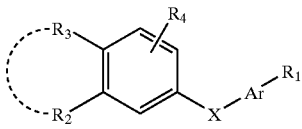

in which:
Ar is an aromatic divalent radical optionally substituted by an $R_5$ radical or a heteroaromatic divalent radical optionally substituted by an $R_6$ radical when the heteroatom is nitrogen,
$R_1$ represents H, —$CH_3$, —$CH_2OR_6$, —$OR_6$, —$COR_7$ or —$S(O)_tR_9$, t being 0, 1 or 2,
$R_2$ and $R_3$ represent H, $C_1$–$C_{20}$ alkyl, —$OR_6$ or —$SR_6$, or $R_2$ and $R_3$, taken together, form a 5- or 6-membered ring optionally substituted by methyl groups and/or optionally interrupted by an oxygen or sulphur atom,
$R_4$ and $R_5$ represent H, a halogen, a lower alkyl or —$OR_6$,
$R_6$ represents H, lower alkyl or —$COR_9$,
$R_7$ represents H, lower alkyl,

or —$OR_8$,
$R_8$ represents H, $C_1$–$C_{20}$ alkyl, which can be linear or branched, alkenyl, mono- or polyhydroxyalkyl, optionally substituted aryl or aralkyl, or a sugar or amino acid or peptide residue,
$R_9$ represent lower alkyl,
R and R' represent H, lower alkyl, mono- or polyhydroxyalkyl, optionally substituted aryl or a sugar, amino acid or peptide residue or R and R', taken together, form a heterocycle, and
X represents a divalent radical which, from right to left or vice versa, has the formula:

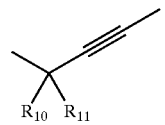

in which:
$R_{10}$ represents H, lower alkyl or —$OR_6$,
$R_{11}$ representing —$OR_6$,
or $R_{10}$ and $R_{11}$, taken together, form an oxo (=O) radical, and the salts of the said compounds of above formula, when $R_1$ represents a carboxylic acid functional group, and the optical and geometrical isomers of these said compounds.

The compounds according to the present invention, with respect to those of EP-601,258, are essentially distinguished in that the —X—Ar—$R_1$ substituent is at the ortho position with respect to the $R_2$ radical or to the 5- or 6-membered ring when $R_2$ and $R_3$ are taken together, whereas, in ES-661,258, the —X—Ar—$R_1$ substituent is found at the meta position.

This is because it has been found, unexpectedly and surprisingly, that this modification in structure makes it possible to significantly increase the pharmaceutical and cosmetic properties thereof and, in addition, to decrease certain side effects thereof.

The subject-matter of the present invention is therefore novel compounds which can be represented by the following general formula:

(I)

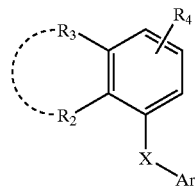

in which:
Ar represents a radical chosen from the following formulae (a) to (c):

(a)

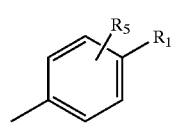

(b)

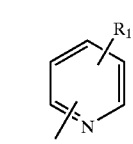

(c)

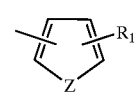

Z being an oxygen or sulphur atom,
$R_1$ represents —$CH_3$, —$CH_2$—O—$R_6$, —$OR_6$ or —$COR_7$, $R_2$ represents —$OR_8$, —$SR_8$ or a polyether radical, if, in the latter case, $R_4$ represents linear or branched $C_1$–$C_{20}$ alkyl and is at the ortho or meta position with respect to the X—Ar bond, $R_3$ represents lower alkyl, or $R_2$ and $R_3$, taken together, form a 5- or 6-membered ring optionally substituted by at least one methyl and/or optionally interrupted by an oxygen or sulphur atom, $R_4$ represents H, a halogen, linear or branched $C_1$–$C_{20}$ alkyl, —$OR_8$, a polyether radical or aryl, $R_5$ represents H, a halogen, linear or branched $C_1$–$C_{20}$ alkyl or an —$OR_8$ radical, $R_6$ represents H, lower alkyl or a —$COR_9$ radical, $R_7$ represents H, lower alkyl,

or —$OR_{10}$, $R_8$ represents H, lower alkyl or —$COR_9$, $R_9$ represents lower alkyl, $R_{10}$ represents H, $C_1$–$C_{20}$ alkyl, which can be linear or branched, alkenyl, mono- or polyhydroxyalkyl, optionally substituted aryl or aralkyl, or a sugar residue, r' and r" represent H, lower alkyl, mono- or polyhydroxyalkyl, optionally substituted aryl, or an amino acid or sugar residue or, taken together with the nitrogen atom, form a heterocycle, X represents a divalent radical which, from right to left or vice versa, has the formula:

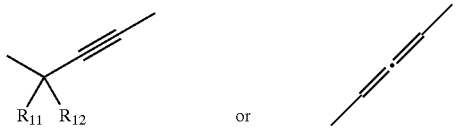

$R_{11}$ representing H or —$OR_6$, $R_6$ having the same meaning as above, $R_{12}$ representing H or lower alkyl, or $R_{11}$ and $R_{12}$, taken together, form an oxo (=O) radical, and the sales of the compounds of formula (I), when $R_1$ represents a carboxylic acid functional group, and the optical and geometrical isomers of the said compounds of formula (I).

When the compounds according to the invention are provided in the form of a salt, it is preferably a salt of an alkali metal or alkaline earth metal or alternatively of zinc or of an organic amine.

According to the present invention, lower alkyl is understood to mean a $C_1$–$C_6$ radical, preferably the methyl, ethyl, isopropyl, butyl, tert-butyl and hexyl radicals.

$C_1$–$C_{20}$ alkyl, which can be linear or branched, is understood to mean in particular the methyl, ethyl, propyl, isopropyl, hexyl, heptyl, 2-ethylhexyl, octyl, nonyl, dodecyl, hexadecyl and octadecyl radicals.

Monohydroxyalkyl is understood to mean a radical preferably having 2 or 3 carbon atoms, in particular a 2-hydroxyethyl, 2-hydroxypropyl or 3-hydroxypropyl radical.

Polyhydroxyalkyl is understood to mean a radical preferably having 3 to 6 carbon atoms and from 2 to 5 hydroxyl groups, such as the 2,3-dihydroxypropyl, 2,3,4-trihydroxybutyl or 2,3,4,5-tetrahydroxy-pentyl radicals or the pentaerythritol residue.

Polyether radical is understood to mean a radical having from 1 to 6 carbon atoms and from 1 to 3 oxygen or sulphur atoms, such as the methoxymethyl ether, methoxyethoxymethyl ether or methylthiomethyl ether radicals.

Aryl is understood to mean a pyridyl radical, a thiophenyl radical or a phenyl radical optionally substituted by at least one halogen atom, one hydroxyl, one nitro functional group, one lower alkyl, one $CF_3$ radical, one amino radical optionally protected by an acetyl functional group or optionally substituted by one or two lower alkyl(s), one alkoxy radical or one polyether radical. Aryl is preferably understood to mean a phenyl radical optionally substituted by at least one halogen atom, one hydroxyl, one nitro functional group, one lower alkyl, one $CF_3$ radical, one amino radical optionally protected by an acetyl functional group or optionally substituted by one or two lower alkyl(s), one alkoxy radical or one polyether radical, the latter being as defined above.

When the substituent is an alkoxy radical, the latter is preferably a $C_1$–$C_{12}$ alkoxy radical, such as in particular the methoxy, ethoxy, propyloxy, isopropyloxy, hexyloxy, heptyloxy, octyloxy and nonyloxy radicals.

Aralkyl is preferably understood to mean the benzyl or phenethyl radical optionally substituted by at least one halogen atom, one hydroxyl or one nitro functional group.

Alkenyl is understood to mean a radical preferably having 2 to 5 carbon atoms and exhibiting one or more ethylenic unsaturations, such as more particularly the allyl radical.

Sugar residue is understood to mean a residue deriving in particular from glucose, galactose, mannose or glucuronic acid.

Amino acid residue is understood to mean in particular a residue deriving from lysine, glycine or aspartic acid and peptide residue is understood to mean more particularly a dipeptide or tripeptide residue resulting from the combination of amino acids.

Heterocycle is preferably understood to mean a piperidino radical, a morpholino radical, a pyrrolidino radical or a piperazino radical optionally substituted at the 4-position by a lower $C_1$–$C_5$ alkyl or a mono- or polyhydroxyalkyl, as defined above.

When $R_4$ and $R_5$ represent a halogen, the latter is preferably a fluorine, chlorine or bromine atom.

According to a preferred embodiment, the compounds according to the invention correspond to the following general formula:

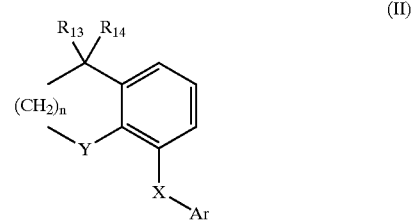

(II)

in which:

Ar represents a radical of following formula (a) or (b):

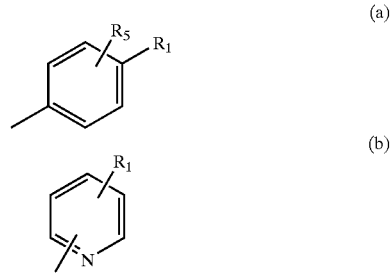

$R_1$ represents —$COR_7$, $R_5$ and $R_7$ being as defined above for the formula (I), X represents a divalent radical which, from right to left or vice versa, has the formula:

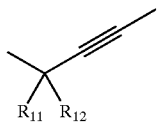

$R_{11}$ and $R_{12}$ represent H, $R_{13}$ and $R_{14}$, which are identical or different, represent H or —$CH_3$, Y represents an oxygen or sulphur atom or a methylene, ethylidene or isopropylidene divalent radical, and n is 1 or 2.

Mention may in particular be made, among the compounds corresponding to the above formulae (I) and (II) according to the present invention, of the following:

Methyl 2-hydroxy-4-[3-(4,4-dimethylchroman-8-yl)prop-1-ynyl]benzoate,

2-Hydroxy-4-[3-(4,4-dimethylchroman-8-yl)-prop-1-ynyl]benzoic acid,

Methyl 2-hydroxy-4-[3-hydroxy-3-(4,4-dimethylchroman-8-yl)prop-1-ynyl]benzoate,

2-Hydroxy-4-[3-hydroxy-3-(4,4-dimethylchroman-8-yl)prop-1-ynyl]benzoic acid,

Methyl 2-hydroxy-4-[3-(4,4-dimethylthiochroman-8-yl)prop-1-ynyl]benzoate,

2-Hydroxy-4-[3-(4,4-dimethylthiochroman-8-yl)prop-1-ynyl]benzoic acid,

Ethyl 4-[3-hydroxy-3-(5,5,8,8-tetramethyl-3-phenyl-5,6,7,8-tetrahydronaphth-1-yl)prop-1-ynyl]-benzoate, 4-[3-Hydroxy-3-(5,5,8,8-tetramethyl-3-phenyl-5,6,7,8-tetrahydronaphth-1-yl)prop-1-ynyl]benzoic acid, 4-[3-(5,5,8,8-Tetramethyl-3-phenyl-5,6,7,8-tetrahydronaphth-1-yl)prop-1-ynyl]benzoic acid, Ethyl 4-[3-(4,4-dimethylthiochroman-5-yl)-3-hydroxyprop-1-ynyl]benzoate, 4-[3-(4,4-Dimethylthiochroman-5-yl)-3-hydroxyprop-1-ynyl]benzoic acid, 4-[3-(4,4-Dimethylthiochroman-5-yl)prop-1-ynyl]benzoic acid, Ethyl 4-[3-(3,5-di-tert-butyl-2-(methoxymethoxy)phenyl)-3-hydroxyprop-1-ynyl]benzoate, 4-[3-(3,5-D-tert-butyl-2-(methoxymethoxy)-phenyl)-3-hydroxyprop-1-ynyl]benzoate, Ethyl 4-[3-(3,5-di-tert-butyl-2-hydroxyphenyl)-3-hydroxyprop-1-ynyl]benzoate, Ethyl-4-[3-(3,5-di-tert-butyl-2-hydroxyphenyl)prop-1-ynyl]benzoate, Ethyl-4-[3-(3,5-di-tert-butyl-2-methoxyphenyl)-3-hydroxyprop-1-ynyl]benzoate, 4-[3-(3,5-Di-tert-butyl-2-methoxyphenyl)-3-hydroxyprop-1-ynyl]benzoic acid, 4-[3-(3,5-Di-tert-butyl-2-methoxyphenyl)prop-1-ynyl]benzoic acid, Ethyl 4-[3-(5-tert-butyl-4-(methoxymethoxy)-biphenyl-3-yl)-3-hydroxyprop-1-ynyl]benzoate, 4-[3-(5-tert-Butyl-4-(methoxymethoxy)-biphenyl-3-yl)-3-hydroxyprop-1-ynyl]benzoic acid, Ethyl 4-[4-(5-tert-butyl-4-methoxybiphenyl-3-yl)3-hydroxyprop-1-ynyl]benzoate, 4-[3-(5-tert-Butyl-4-methoxybiphenyl-3-yl)-3-hydroxyprop-1-ynyl]benzoic acid, Ethyl 4-[3-(3,5-di-tert-butyl-2-methoxy-phenyl)-3-methoxyprop-1-ynyl]benzoate, 4-[3-(3,5-Di-tert-butyl-2-methoxyphenyl)-3-methoxyprop-1-ynyl]benzoic acid, Methyl 4-[3-(4,4-dimethylthiochroman-8-yl)-prop-1-ynyl]benzoate, Ethyl 6-[3-(4,4-dimethylthiochroman-8-yl)-prop-1-ynyl]nicotinate, 4-[3-(4,4-Dimethylthiochroman-8-yl)prop-1-ynyl]benzaldehyde, 4-[3-(4,4-Dimethylthiochroman-8-yl)prop-1-ynyl]phenol, Ethyl 4-[3-(5-tert-butyl-4-hydroxybiphenyl-3-yl)-3-hydroxyprop-1-ynyl]benzoate, 4-[3-(5-tert-Butyl-4-methoxybiphenyl-3-yl)prop-1-ynyl]benzoic acid, 4-[3-(4,4-Dimethylthiochroman-8-yl)prop-1-ynyl]benzoic acid, 4-[3-(5,6,7,8-Tetrahydro-5,5,8,8-tetramethyl-1-naphthyl)prop-1-ynyl]benzoic acid, 2-Hydroxy-4-[3-(5,6,7,8-tetrahydro-5,5,8,8-tetramethyl-1-naphthyl)prop-1-ynyl]benzoic acid, Methyl 2-hydroxy-4-[3-hydroxy-3-(4,4-dimethylchroman-8-yl)prop-1-ynyl]benzoate, 2-Hydroxy-4-[3-hydroxy-3-(4,4-dimethylchroman-8-yl)prop-1-ynyl]benzoic acid, 2-Hydroxy-4-[3-(4,4-dimethylthiochroman-8-yl)prop-1-ynyl]benzoic acid, 4-[3-(4,4-Dimethylthiochroman-8-yl)prop-1-ynyl]benzamide, N-Ethyl-4-[3-(4,4-dimethylthiochroman-8-yl)prop-1-ynyl]benzamide, N-(4-Hydroxyphenyl)-4-[3-(4,4-dimethylthiochroman-8-yl)prop-1-ynyl]benzamide, 4-[3-(4,4-Dimethylthiochroman-8-yl)prop-1-ynyl]benzoic acid morpholide, 4-[3-(4,4-Dimethylthiochroman-8-yl)prop-2-ynyl]benzoic acid, 4-[3-(5,5,8,8-Tetramethyl-5,6,7,8-tetrahydronaphth-1-yl)prop-2-ynyl]benzoic acid, 4-[3-(4,4-Dimethyl-6-phenylthiochroman-8-yl)prop-1-ynyl]benzoic acid, 4-[3-(4,4-Dimethyl-6-phenylchroman-8-yl)prop-1-ynyl]benzoic acid, 4-[3-(4,4-Dimethyl-6-phenylthiochroman-8-yl)prop-2-ynyl]benzoic acid, 4-[3-(4,4-Dimethyl-6-(p-tolyl)thiochroman-8-yl)prop-1-ynyl]benzoic acid, 4-[3-(5,5,8,8-Tetramethyl-5,6,7,8-tetrahydronaphth-1-yl)prop-2-ynyl]benzoic acid, 4-[3-(5,5,8,8-Tetramethyl-3-(p-tolyl)-5,6,7,8-tetrahydronaphth-1-yl)prop-1-ynyl]benzoic acid, 4-(3-[3-(4-Methoxyphenyl)-5,5,8,8-tetramethyl-5,6,7,8-tetrahydronaphth-1-yl]prop-1-ynyl)-benzoic acid, 2-Hydroxy-4-[3-(5,5,8,8-tetramethyl-3-(p-tolyl)-5,6,7,8-tetrahydronaphth-1-yl)prop-1-ynyl]-benzoic acid, and 3-Hydroxy-4-[3-(5,5,8,8,-tetramethyl-3-phenyl-5,6,7,8-tetrahydronaphth-1-yl)prop-1-ynyl]benzoic acid.

Another subject-matter of the present invention is the processes for the preparation of the compounds of formula (I) above according to the reaction scheme given in Table A.

TABLE A
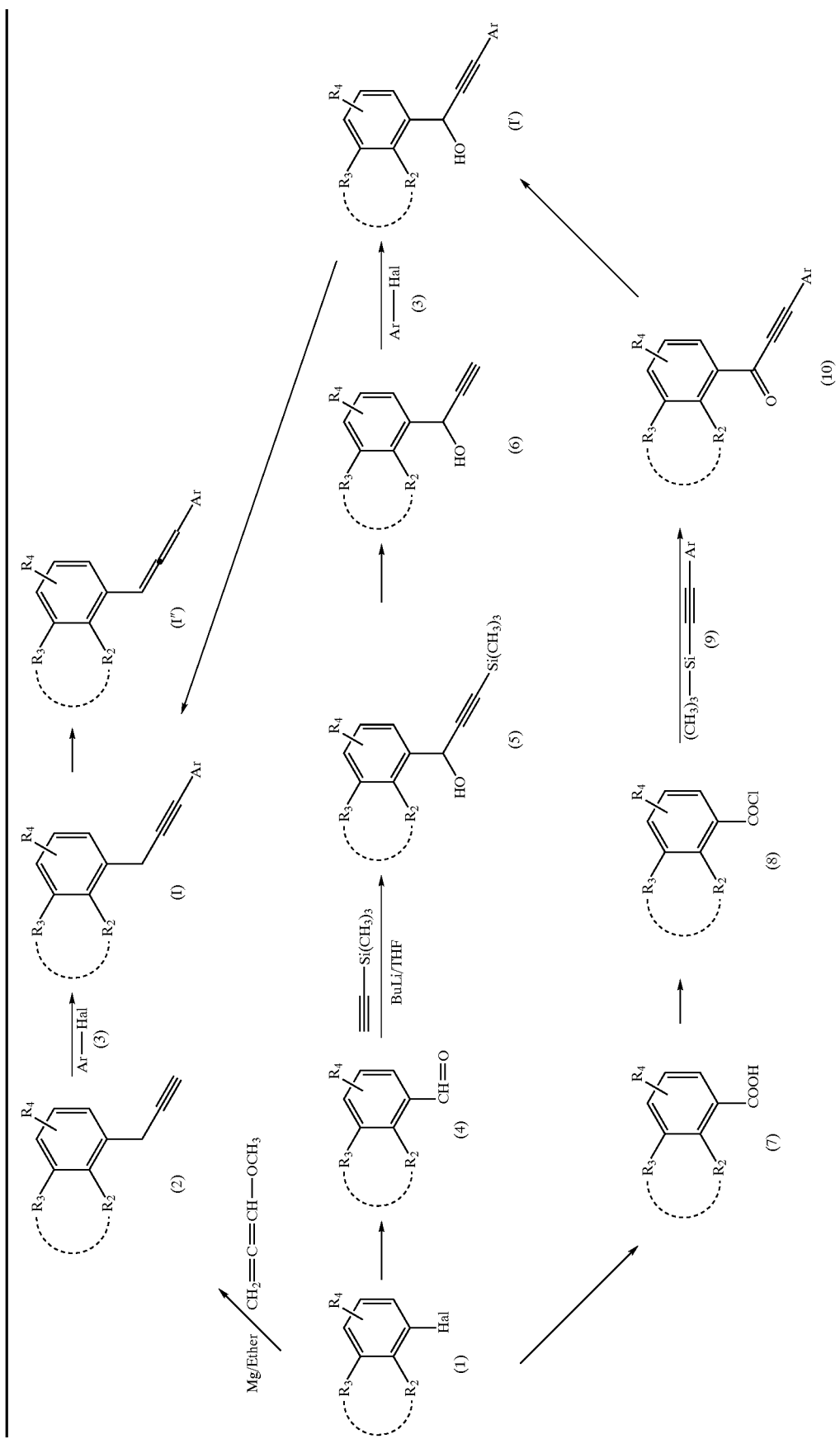

The compounds of formula (I) can be prepared from a halogenated derivative (1), preferably a brominated or iodinated derivative, by conversion into the magnesium derivative, then reaction with methoxyallene in the presence of CuBr and production of the propargyl derivative (2). The latter is subsequently coupled with a halogenated derivative (3), preferably an iodinated or brominated derivative, in the presence of a palladium catalyst, for example bis(triphenylphosphine)palladium(II) chloride, in a solvent, such as triethylamine.

The compounds of formula (I) can also be prepared by a sequence of reactions comprising the reaction of lithium trimethylsilylacetylide with an aldehyde compound (4) and deprotection with tetrabutyl-ammonium fluoride in THF, producing the propargyl alcohol (6). By coupling of the latter with a halogenated derivative (3), preferably an iodinated or brominated derivative, in the presence of a palladium catalyst, for example bis(triphenylphosphine)palladium(II) chloride, in a solvent, such as triethylamine, the hydroxylated compound according to the invention of formula (I') is obtained. The latter, by reduction of the alcohol functional group to carbide in the presence of trimethylsilyl iodide in a solvent, such as hexane, or by hydride transfer from a silane, such as triethylsilane, in the present of $BF_3 \cdot Et_2O$ in a chlorinated solvent, such as methylene chloride, results in the compound of formula (I).

The compounds of formula (I) can also be prepared by a sequence of reactions comprising the reaction of a benzoyl chloride of formula (8) with an acetylenic derivative of formula (9) in the presence of a Lewis acid (for example $AlCl_3$) in a chlorinated solvent, such as dichloromethane. The acetylenic ketone (10) thus obtained is reduced to the hydroxylated compound according to the invention (I') by the action of an alkali metal hydride, such as sodium borohydride, in an alcoholic solvent (for example methanol). The reduction of the alcohol functional group of (I') to carbide is carried out as above and results in the compound of formula (I).

The allene compounds of formula (I") can be prepared by heating the compounds of formula (I) in the presence of a base (NaOH, $Et_3N$, DBU) in a solvent, such as heptane or THF.

The starting materials for the synthesis of the preferred compounds or formula (II) can be obtained according to different reaction schemes depending on the meaning of the Y radical.

When Y represents a sulphur atom, $R_{13}$ and $R_{14}$ representing —$CH_3$ and n=2, that is to say 4,4-dimethylthiochromanyl derivatives, the latter can be obtained from 2-bromothiophenol by coupling with 4-bromo-2-methyl-2-butene in the presence of potassium carbonate or sodium hydride in DMF and then cyclization, either in the presence of p-toluenesulphonic acid or in the presence of aluminium chloride or of polyphosphoric acid, according to the following reaction scheme:

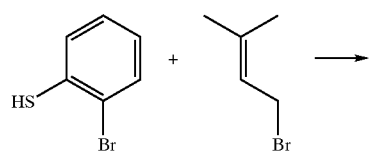

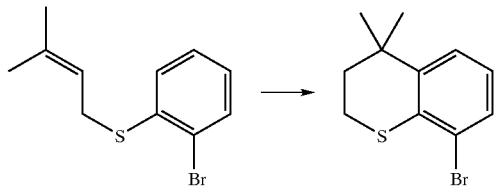

When Y represents an oxygen atom, $R_{13}$ and $R_{14}$ representing —$CH_3$ and n=2, that is to say 4,4-dimethylchromanyl derivatives, the latter can be obtained from phenol by reaction with 3-methyl-3-buten-1-yl diphenyl phosphate in the presence of stannic chloride, then lithiation in the presence of butyllithium and of tetramethylethylenediamine and reaction with diiodomethane (K. McWilliams, J. Org. Chem., 1966, 61, 7408–14), according to the following reaction scheme:

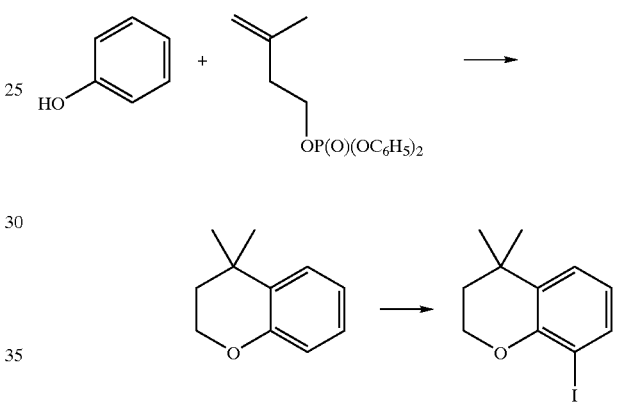

When Y represents an isopropylidene radical, $R_{13}$ and $R_{14}$ representing —$CH_3$ and n=2, that is to say tetrahydrotetramethylnaphthyl derivatives, the latter can be obtained from 3-bromophenol by reaction with 2,5-dichloro-2,5-dimethylhexane in the presence of aluminium chloride, then hydrogenolysis in the presence of palladium-on-charcoal and of formic acid or of hydrogen and formation of the triflate derivative, and then hydroformylation (H. Kotsuki, Synthesis, 1996, 470-2), according to the following reaction scheme:

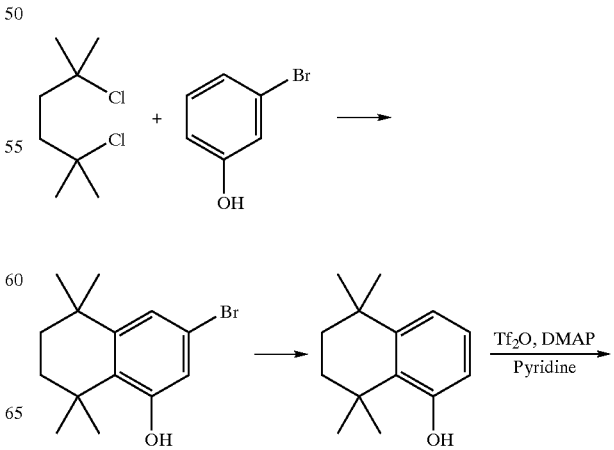

-continued

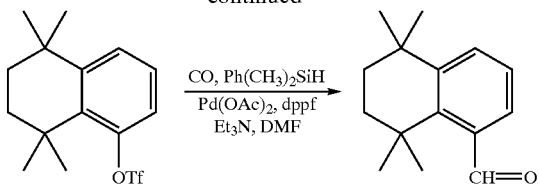

When Y represents a methylene radical $R_{13}$ and $R_{14}$ representing —$CH_3$ and n=2, that is to say tetrahydrodimethylnaphthyl derivatives, the latter can be obtained from 2-bromoanisole by coupling with the zinc derivative of 1-bromo-4-methylpent-3-ene in the presence of a palladium catalyst, for example $PdCl_2$/(dppf) (R. L. Danheiser, J. Org. Chem., 1995, 60, 8341–8350), then cyclization in the presence of a Lewis acid, for example aluminium chloride, then demethylation with $BBr_3$, formation of the triflate and hydroformylation as described above.

This sequence of reactions can be represented by the following reaction scheme:

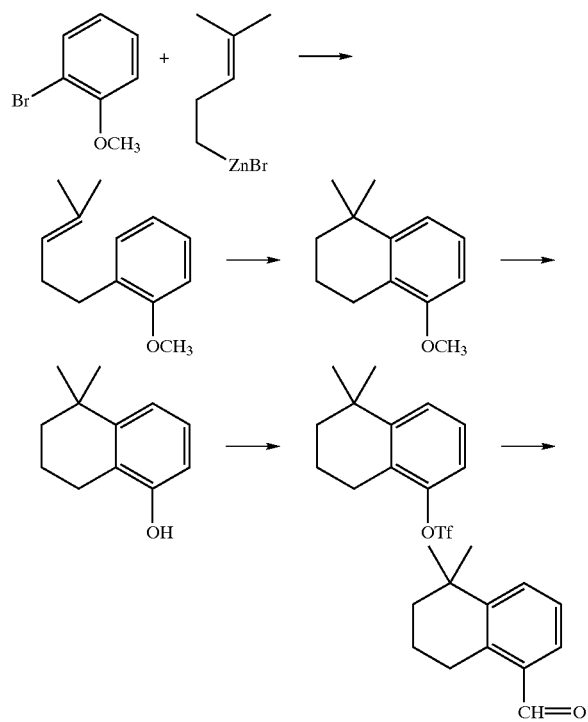

When $R_1$ represents —COOH, the compounds are prepared while protecting $R_1$ with a protective group of alkyl, allyl or tert-butyl type.

Conversion to the free form can be carried out:

in the case of an alkyl protective group, by means of sodium hydroxide or lithium hydroxide in an alcoholic solvent, such as methanol, or in THF;

in the case of an allyl protective group, by means of a catalyst, such as certain transition metal complexes, in the presence or a secondary amine, such as morpholine;

in the case of a protective group of tert-butyl type, by means or trimethylsilyl iodide.

When $R_1$ is —CH, the compounds can be obtained from the corresponding acid by reduction in the presence of lithium aluminium hydride.

When $R_1$ is

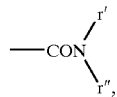

the compounds can be obtained by conversion of the corresponding acid to the acid chloride, for example with thionyl chloride, and then reaction with ammonia or an appropriate amine.

Another subject-matter of the present invention is, as medicament, the compounds of formula (I) as defined above.

These compounds exhibit activity in the test for differentiation of mouse embryonic teratocarcinoma cells (F9) (Cancer Research, 43, p. 5268, 1983) and/or in the test for inhibition of ornithine decarboxylase after induction with TPA in mice (Cancer Research, 38; p. 793–801, 1978). These tests show the activities of the compounds in the fields of cell differentiation and proliferation respectively.

In the test for differentiation of the cells (F9), it is possible to evaluate an agonist activity, like an antagonist activity, at the retinoic acid receptors. This is because an antagonist is inactive when it is alone in this test but partially or completely inhibits the effect produced by an agonist retinoid on the morphology and on the secretion of the plasminogen activator. These compounds therefore also exhibit activity in a test which consists in identifying RAR-antagonist molecules, as described in French Patent Application No. 95-07302, filed on 19 Jun. 1995 by the Applicant Company. This test comprises the following stages: (i) a sufficient amount of an RAR-agonist molecule is applied topically to part of the skin of a mammal, (II) a molecule capable of exhibiting an RAR-antagonist activity is administered systemically or topically to the same mammal or to the same part of the skin of the mammal, before, during or after stage (i), and (iii) the response on the part of the skin thus treated of the mammal is evaluated. Thus, the response to a topical application to the ear of a mammal of an RAR-agonist molecule, which corresponds to an increase in the thickness of this ear, can be inhibited by the systemic or topical administration of an RAR-antagonist molecule.

The compounds according to the invention are particularly well suited to the following fields of treatment:

1) for treating dermatological conditions linked to a disorder of keratinization involving differentiation and proliferation, in particular for treating acne vulgaris, comedonic or polymorphic acne, acne rosacea, nodulocystic acne, acne conglobata, senile acne and secondary acnes such as solar, drug or occupational acne, 2) for treating other types of disorders of keratinization, in particular ichthyoses, ichthyosiform conditions, Darier's disease, palmoplantar keratoderma, leucoplakia and leucoplakiform conditions or cutaneous or mucosal (oral) lichen, 3) for treating other dermatological conditions linked to a disorder of keratinization with an inflammatory and/or immunoallergic component and, in particular, all forms of psoriasis, whether cutaneous, mucosal or ungual, and even psoriatic rheumatism, or alternatively cutaneous atopy, such as eczema, or respiratory atopy or alternatively gingival hypertrophy; the compounds can also be used in certain inflammatory conditions which do not show disorder of keratinization, 4) for treating all dermal or epidermal proliferations, whether they are benign or malignant and whether they are or are not of viral origin, such as common warts, flat warts and epidermodysplasia verruciformis, florid or oral papillomatoses and the proliferations which can be induced by ultraviolet radiation, in particular in the case of basal cell and prickle cell epithelioma, 5) for treating other dermatological disorders, such as bullous dermatoses and collagen diseases, 6) for treating certain ophthalmological disorders, in particular corneopathies, 7) for repairing or combating skin ageing, whether photoinduced or chronologic, or for reducing actinic keratoses and pigmentations or any pathology associated with chronologic or actinic ageing, 8) for preventing or treating the stigmata of epidermal and/or dermal atrophy induced by local or systemic corticosteroids, or any other form of cutaneous atrophy, 9) for preventing or treating disorders of cicatrization or for preventing or for repairing stretch marks, 10) for combating disorders of the sebaceous function, such as hyperseborrhoea of acne or simple seborrhoea, 11) for treating or preventing cancerous or precancerous conditions, 12) for treating inflammatory conditions, such as arthritis, 13) for treating any condition of viral origin at the cutaneous level or the general level, 14) for preventing or treating alopecia, 15) for treating dermatological or general conditions with an immunological component, and 16) for treating conditions of the cardiovascular system, such as arteriosclerosis.

In the therapeutic fields mentioned above, the compounds according to the invention can advantageously be employed in combination with other compounds with an activity of retinoid type, with vitamins D or their derivatives, with corticosteroids, with agents for combating free radicals, with α-hydroxy or α-keto acids or their derivatives, or alternatively with ion-channel blockers. Vitamins D or their derivatives is understood to mean, for example, the derivatives of vitamin $D_2$ or $D_3$ and in particular 1,25-dihydroxyvitamin $D_3$. Agents for combating free radicals is understood to mean, for example, α-tocopherol, superoxide dismutase or SOD, ubiquinol or certain metal-chelating agents. α-Hydroxy or α-keto acids or their derivatives is understood to mean, for example, lactic acid, malic acid, citric acid, glycolic acid, mandelic acid, tartaric acid, glyceric acid or ascorbic acid or their salts, amides or esters. Finally, ion-channel blockers is understood to mean, for example, minoxidil (2,4-diamino-6-piperidinopyrimidine 3-oxide) and its derivatives.

Another subject-matter of the present invention is pharmaceutical compositions comprising at least one compound of formula (I) as defined hereinabove, one of its optical or geometrical isomers or one of its salts.

The pharmaceutical compositions are intended especially for treating the abovementioned conditions and are characterized in that they comprise, in a pharmaceutically acceptable vehicle which is compatible with the method of administration selected, at least one compound of formula (I), one of its optical or geometrical isomers or one of its salts.

The administration of the compounds according to the invention can be carried out enterally, parenterally, topically or ocularly.

For enteral administration, the compositions can be provided in the form of tablets, hard gelatin capsules, dragées, syrups, suspensions, solutions, powders, granules, emulsions or polymeric or lipid vesicles or nanospheres or microspheres which make possible controlled release. For parenteral administration, the compositions car be provided in the form of solutions or suspensions for infusion or for injection.

The compounds according to the invention are generally administered at a daily dose of approximately 0.01 mg/kg to 100 mg/kg by body weight, and this at the rate of 1 to 3 intakes.

For topical administration, the pharmaceutical compositions based on the compounds according to the invention are more particularly intended for treating the skin and the mucous membranes and can then be provided in the form of ointments, creams, milks, salves, powders, impregnated pads, solutions, gels, sprays, lotions or suspensions. They can also be provided in the form of polymeric or lipid vesicles or nanospheres or microspheres or of polymeric patches and of hydrogels which make possible controlled release of the active principle. These compositions for topical administration can furthermore be provided either in anhydrous form or in aqueous form, according to the clinical indication.

For ocular administration, they are mainly eye washes.

These compositions for topical or ocular use contain at least one compound of formula (I) as defined above or one of its optical or geometrical isomers or one of its salts, at a concentration preferably of between 0.001% and 5% by weight with respect to the total weight of the composition.

The compounds of formula (I) according to the invention also find an application in the cosmetics field, in particular in body and hair hygiene, and especially for the treatment of skin with a tendency to develop acne, for hair regrowth and combating hair loss, for combating the greasy appearance of the skin or the hair, in protecting against the deleterious effects of sunlight or in the treatment of physiologically dry skin, and for preventing and/or for combating photoinduced or chronologic ageing.

In the cosmetics field, the compounds according to the invention can furthermore be advantageously employed in combination with other compounds with an activity of retinoid type, with D vitamins or their derivatives, with corticosteroids, with agents for combating free radicals, with α-hydroxy or α-keto acids or their derivatives, or alternatively with ion-channel blockers, all the latter compounds being as defined above.

Another subject matter of the present invention is thus a cosmetic composition which is characterized in that it comprises, in a cosmetically acceptable vehicle, at least one compound of formula (I) as defined above or one of its optical or geometrical isomers or one of its salts, it being possible for the said cosmetic composition to be provided in particular in the form of a cream, a milk, a lotion, a gel, polymeric or lipid vesicles or nanospheres or microspheres, a soap or a shampoo.

The concentration of compound of formula (I) in the cosmetic compositions according to the invention is advantageously between 0.001% and 3% by weight with respect to the total weight of the composition.

The pharmaceutical and cosmetic compositions according to the invention can additionally contain inert or even pharmacodynamically or cosmetically active additives or combinations of these additives and especially: wetting agents; depigmenting agents, such as hydroquinone, azelaic acid, caffeic acid or kojic acid; emollients; hydrating agents, such as glycerol, PEG 400, thiamorpholinone and its derivatives or urea; anti-seborrhoeic or anti-acne agents, such as S-carboxymethylcysteine, S-benzylcysteamine, their salts or their derivatives, or benzoyl peroxide; antibiotics, such as erythromycin and its esters, neomycin, clindamycin and its esters, or tetracyclins; antifungal agents, such as ketoconazole or 4,5-polymethylene-3-isothiazolidones; agents promoting hair regrowth, such as minoxidil (2,4-diamino-6- piperidinopyrimidine 3-oxide) and its derivatives, diazoxide (7-chloro-3-methyl-1,2,4-benzothiadiazine 1,1-dioxide) and phenytoin (5,5-diphenylimidazolidine-2,4-dione); non-steroidal anti-inflammatory agents; carotenoids and especially β-carotene; anti-psoriatic agents, such as anthralin and its derivatives; and finally eicosa-5,8,11,14-tetraynoic and eicosa-5,8,11-triynoic acids, their esters and amides.

The compositions according to the invention can also contain flavour enhancers, preserving agents such as the esters of para-hydroxybenzoic acid, stabilizing agents, moisture-regulating agents, pH-regulating agents, osmotic-pressure-modifying agents, emulsifying agents, UV-A and UV-B screening agents and antioxidants such as α-tocopherol, butylated hydroxyanisole or butylated hydroxytoluene.

A number of examples of the preparation of active compounds of formula (I) according to the invention, as well as various pharmaceutical and cosmetic formulations based on these compounds, will now be given by way of illustration and without any implied limitation.

EXAMPLE 1

Methyl 2-hydroxy-4-[3-(4,4-dimethylchroman-8-yl) prop-1-ynyl]benzoate (a) 4,4-dimethyl-8-iodochroman 2.00 g (12.3 mmol) of 4,4-dimethylchroman and 30 ml of ethyl ether are introduced into a three-necked flask under argon. 2.4 m (15.9 mmol) of tetramethylethylenediamine (TMEDA) are added dropwise, the mixture is cooled to −78° C. and 5.9 ml (14.8 mmol) of n-butyllithium (2.5M in hexane) are added dropwise. The temperature is allowed to return to −20 °C. over two hours and then to room temperature and the mixture is stirred for 12 hours. 1.3 ml (16.0 mmol) of diiodomethane and 15 ml of ethyl ether are introduced into another three-necked flask under argon. Cooling is carried out to 0° C. and the preceding solution, cooled beforehand to −78° C., is introduced, then the reaction mixture is allowed to return to room temperature and stirred for 12 hours. The reaction mixture is poured into water and extracted with ethyl ether and the organic phase is separated by settling, dried over magnesium sulphate and evaporated. The residue obtained is purified by chromatography on a silica column eluted with heptane. After evaporating the solvents, 1.30 g (37%) of the expected compound are collected in the form of a pale-yellow oil.

$^1$H NMR (CDCl$_3$) δ 1.32 (s, 6H), 1.84 (t, 2H, J=5.4 Hz), 4.28 (t, 2H, J=5.4 Hz), 6.62 (t, 1H, J=7.7 Hz), 7.24 (dd, 1H, J=7.8/1.5 Hz), 7.56 (dd, 1H, J=7.7/1.5 Hz).

(b) Methoxyallene 210 ml (2.5 mol) of propargyl methyl ether and 12.00 g (110.0 mmol) of potassium tert-butoxide are introduced into a three-necked flask under argon. The reaction mixture is heated at reflux for three hours and is distilled at atmospheric pressure. The fraction distilling at 51° C. is collected in order to obtain 153.50 g (88%) of the expected compound in the form of a colourless oil.

$^1$H NMR (CDCl$_3$) δ 3.41 (s, 3H), 5.48 (d, 2H, J=5.9 Hz), 6.77 (t, 1H, J=5.9 Hz).

(c) 3-(4,4-dimethylchroman-8-yl)prop-1-yne 280 mg (11.5 mmol) of magnesium, activated with 1 drop of dibromoethane, are introduced into a three-necked flask under argon. A solution of 3.00 g (10.4 mmol) of 4,4-dimethyl-8-iodochroman in 15 ml of ethyl ether is added dropwise, so as to maintain the reflux of the solvent, and the reaction mixture is stirred at 35° C. for 15 minutes. It is subsequently cooled to −5° C., 40 mg (0.2 mmol) of CuI are added and a solution composed of 1.24 g (17.7 mmol) of methoxyallene in 5 ml of ethyl ether is introduced dropwise. The mixture is stirred for one hour at −5° C., allowed to return to room temperature and stirred for two hours. The reaction mixture is poured into a saturated ammonium chloride solution and extracted with ethyl acetate and the organic phase is separated by settling, dried over magnesium sulphate and evaporated. The residue obtained is purified by chromatography on a silica column eluted with heptane. After evaporating the solvents, 1.30 g (65%) of the expected compound are collected in the form of a yellow oil.

$^1$H NMR (CDCl$_3$) δ 1.33 (s, 6H), 1.83 (t, 2H, J=5.4 Hz), 2.15 (t, 1H, J=2.7 Hz), 3.52 (d, 2H, J=2.7 Hz), 4.21 (t, 2H, J=5.4 Hz), 6.87 (t, 1H, J=7.6 Hz), 7.18 (dd, 1H, J=7.9/1.5 Hz), 7.33 (dd, 1H, J=7.4/1.5 Hz).

(d) Methyl 2-hydroxy-4-[3-(4,4-dimethylchroman-8-yl)-prop-1-ynyl]benzoate 1.18 g (5.9 mmol) of 3-(4,4-dimethylchroman-8-yl)-1-propyne, 1.60 g (5.9 mmol) of methyl 2-hydroxy-4-iodobenzoate and 60 ml of triethylamine are introduced into a three-necked flask under argon. The reaction mixture is degassed by sparging with nitrogen, 332 mg (0.46 mmol) of bis(triphenylphosphine) palladium(II) chloride and 134 mg of copper iodide are introduced and the mixture is stirred at room temperature for eight hours. The reaction mixture is evaporated to dryness, the residue is taken up in ethyl acetate and hydrochloric acid (1N), and the organic phase is separated by settling, dried over magnesium sulphate and evaporated. The residue is purified by chromatography on a silica column eluted with heptane. After evaporating the solvents, an oil, which slowly crystallizes, is obtained and is recrystallized from heptane. 1.00 g (50%) of methyl 2-hydroxy-4-[3-(4,4-dimethylchroman-8-yl)prop-1-ynyl]benzoate is collected in the form of a white solid with a melting point of 92–93° C.

$^1$H NMR (CDCl$_3$) δ 1.34 (s, 6H), 1.8 (t, 2H, J=5.4 Hz), 3.75 (s, 2H), 3.94 (s, 3H), 4.23 (t, 2H, J=5.4 Hz), 6.89 (t, 1H, J=7.6 Hz), 6.95 (dd, 1H, J=8.2/1.5 Hz), 7.06 (d, 1H, J=1.4 Hz), 7.20 (d, 1H, J=6.3 Hz), 7.35 (d, 1H, J=7.4 Hz), 7.75 (d, 1H, J=8.2 Hz), 10.73 (s, 1H).

EXAMPLE 2

2-Hydroxy-4-[3-(4,4-dimethylchroman-8-yl)prop-1-ynyl]-benzoic Acid 860 mg (2.5 mmol) of the methyl ester obtained in Example 1(d), 1.00 g (25.0 mmol) of lithium hydroxide and 50 ml of THF are introduced into a round-bottomed flask. The reaction mixture is heated at reflux for 18 hours and is evaporated to dryness. The residue is taken up in water, acidified to pH 1 and extracted with ethyl ether and the organic phase is separated by settling, dried over magnesium sulphate and evaporated. The residue is triturated in heptane and filtered off and 560 mg (70%) of 2-hydroxy-4-[3-(4,4-dimethylchroman-8-yl)prop-1-ynyl]benzoic acid are collected in the form of a white solid with a melting point of 182–183° C.

$^1$H NMR, (d$_6$-DMSO) δ 1.29 (s, 6H), 1.79 (t, 2H, J=5.2 Hz), 3.72 (s, 2H), 4.20 (t, 2H, J=5.3 Hz), 6.67 (t, 1H, J=7.6 Hz), 6.76 to 6.79 (m, 2H), 7.05 (d, 2H, J=7.6 Hz), 7.55 (d, 1H, J=8.6 Hz).

EXAMPLE 3

Methyl 2-hydroxy-4-[3-hydroxy-3-(4,4-dimethylchroman-8-yl)prop-1-ynyl]benzoate (a) 4,4-dimethylchroman-8-carbaldehyde 14.40 g (50.0 mmol) of 4,4-dimethyl-8-iodochroman and 50 ml of THF are introduced into a three-necked flask under a stream of nitrogen. 22 ml (55.0 mmol) of n-butyllithium (2.5M in hexane) are added dropwise at −78° C., the reaction mixture is stirred for 30 minutes, then 4.2 ml (55.0 mmol) of DMF are added and the mixture is allowed to return to room temperature. The reaction mixture is poured onto an aqueous ammonium chloride solution and extracted with ethyl ether and the organic phase is separated by settling, dried over magnesium sulphate and evaporated. 10.40 g (100%) of the expected compound are collected in the form of a yellow oil.

$^1$NMR (CDCl$_3$) δ 1.36 (s, 6H), 1.86 (t, 2H, J=5.2 Hz), 4.29 (t, 2H, J=5.6 Hz), 6.91 (t, 1H, J=8.4 Hz), 7.50 (dd, 1H, J=7.7/1.7 Hz), 7.64 (dd, 1H, J=7.9/1.7 Hz), 10.42 (s, 1H).

(b) α-ethynyl-4,4-dimethylchroman-8-methanol 7.6 ml (54.0 mmol) of trimethylsilylacetylene and 50 ml of THF are introduced into a three-necked flask. A solution of 22 ml (54.0 mmol) of n-butyllithium (2.5M in hexane) is added dropwise at −78° C. under a stream of nitrogen and the mixture is allowed to return to room temperature. The reaction mixture is introduced dropwise into a cold (−78° C.) solution composed of 9.30 g (49.0 mmol) of 4,4-dimethylchroman-8-carbaldehyde and of 50 ml of THF. The reaction mixture is allowed to return to room temperature, poured onto an aqueous ammonium chloride solution and extracted with ethyl ether and the organic phase is separated by settling, dried over magnesium sulphate and evaporated. 14.00 g (100%) of the expected compound are obtained in the form of a yellow oil. 3.00 g (10.0 mmol) of this oil are mixed with 50 ml of THF, and 11.5 ml (12.6 mmol) of a tetrabutylammonium fluoride solution (1.1M in THF) are added dropwise. The reaction mixture is stirred at room temperature for one hour, is poured into water and extracted with ethyl ether and the organic phase is separated by settling, dried over magnesium sulphate and evaporated. 2.30 g (100%) of the expected compound are collected in the form of a colourless oil.

$^1$H NMR (CDCl$_3$) δ 1.33 (s, 6H), 1.81 to 1.88 (m, 2H), 2.59 (d, 1H, J=2.2 Hz), 4.11 (d, 1H, J=6.1 Hz), 4.25 (t, 2H, J=4.7 Hz), 5.68 (dd, 1H, J=6.1/2.0 Hz), 6.90 (t, 1H, J=7.7 Hz), 7.25 (d, 1H, J=7.8 Hz), 7.41 (d, 1H, J=7.7 Hz).

(c) Methyl 2-hydroxy-4-[3-hydroxy-3-(4,4-dimethylchroman-8-yl)prop-1-ynyl]benzoate 3.00 g (13.9 mmol) of α-ethynyl-4,4-dimethylchroman-8-methanol, 3.90 g (13.9 mmol) of methyl 2-hydroxy-4-iodobenzoate and 100 ml of triethylamine are introduced into a three-necked flask. The reaction mixture is degassed with nitrogen for 30 minutes and then 780 mg (1.1 mmol) of bis(triphenylphosphine)-palladium(II) chloride and 320 mg (1.7 mmol) of copper iodide are successively added. The reaction mixture is stirred at room temperature for 4 hours and is evaporated to dryness and the residue obtained is taken up in water and ethyl ether. The organic phase is separated by settling, dried over magnesium sulphate and evaporated. The residue obtained is purified by chromatography on a silica column eluted with a mixture composed of 50% ethyl acetate and 50% heptane. 2.85 g (56%) of methyl 2-hydroxy-4-[3-hydroxy-3-(4,4-dimethylchroman-8-yl)prop-1-ynyl]benzoate are collected in the form of a white solid with a melting point of 122–123° C.

$^1$H NMR (CDCl$_3$) δ 1.36 (s, 6H), 1.87 to 1.90 (m, 2H), 3.18 (d, 1H, J=6.4 Hz), 3.95 (s, 3H), 4.31 (t, 2H, J=5.3 Hz), 5.86 (d, 1H, J=6.4 Hz), 6.89 to 7.00 (m, 2H), 7.09 (s, 1H), 7.29 (d, 1H, J=7.9 Hz), 7.40 (d, 1H, J=7.4 Hz), 7.77 (d, 1H, J=8.2 Hz).

EXAMPLE 4

2-Hydroxy-4-[3-hydroxy-3-(4,4-dimethylchroman-8-yl)prop-1-ynyl]benzoic Acid 2.80 g (7.6 mmol) of the compound obtained in Example 3(c), 3.20 g (76.5 mmol) of lithium hydroxide and 100 ml of THF are introduced into a round-bottomed flask. The reaction mixture is heated at reflux for 18 hours and evaporated to dryness. The residue is taken up in water, acidified to pH 1 and extracted with ethyl ether and the organic phase is separated by settling, dried over magnesium sulphate and evaporated. The residue is triturated in heptane and filtered off and 660 mg (25%) of 2-hydroxy-4-[3-hydroxy-3-(4,4-dimethylchroman-8-yl) prop-1-ynyl]benzoic acid are collected in the form of a white solid with a melting point of 225–227° C.

1H NMR (CDCl$_3$+2 drops of d$_6$-DMSO) δ 1.34 (s, 6H), 1.87 (t, 2H, J=6.0 Hz), 3.50 (s, 1H), 4.28 (t, 2H, J=5.7 Hz), 5.90 (s, 1H), 6.88 to 6.96 (m, 2H), 7.02 (s, 1H) 7.27 (d, 1H, J=7.8 Hz), 7.46 (d, 1H, J=7.4 Hz), 7.79 (d, 1H, J=8.1 Hz), 11.23 (br s, 1H).

EXAMPLE 5

Methyl 2-hydroxy-4-[3-(4,4-dimethylthiochroman-8-yl)-prop-1-ynyl]benzoate (a) 2-bromo-1-(3-methylbut-2-enylthio)benzene 19.30 g (102.0 mmol) of 2-bromothiophenol, 160 ml of DMF and 15.50 g (112.0 mmol) of potassium carbonate are introduced into a three-necked flask. 13 ml (112.0 mmol) of 1-bromo-3-methyl-2-butene are added dropwise and the reaction mixture is stirred at room temperature for two hours. It is poured into water and extracted with ethyl acetate and the organic phase is separated by settling, washed with water, dried over magnesium sulphate and evaporated. 26.00 g (99%) of the expected compound are collected in the form of an orangey oil.

$^1$H NMR (CDCl$_3$) δ 1.65 (s, 3H), 1.73 (s, 3H), 3.56 (d, 2H, J=7.7 Hz), 5.32 (td, 1H, J=7.7/1.4 Hz), 6.96 to 7.06 (m, 1H), 7.22 to 7.26 (m, 2H), 7.52 (d, 1H, J=7.7 Hz).

(b) 4,4-dimethyl-8-bromothiochroman 26.00 g (102.0 mmol) of 2-bromo-1-(3-methylbut-2-enylthio)benzene, 130 ml of toluene and 23.20 g (122.0 mmol) of para-toluenesulphonic acid are introduced into a three-necked flask. The reaction mixture is heated at reflux for four hours and is evaporated to dryness. The residue is taken up in an aqueous sodium hydrogencarbonate solution and extracted with ethyl acetate and the organic phase is separated by settling, dried over magnesium sulphate and evaporated. The residue obtained is purified by chromatography on a silica column eluted with heptane. 20.00 g (76%) of the expected compound are collected in the form of an orangey oil.

$^1$H NMR (CDCl$_3$) δ 1.33 (s, 6H), 1.94 (t, 2H, J=6.0 Hz), 3.04 (t, 2H, J=6.1 Hz), 6.89 (t, 1H, J=7.9 Hz), 7.34 (d, 2H, J=7.9 Hz).

(c) 3-(4,4-dimethylthiochroman-8-yl)prop-1-yne

In a way analogous to Example 1(c), from 3.00 g (11.7 mmol) of 4,4-dimethyl-8-bromothiochroman, 710 mg (28%) of the expected compound are obtained in the form of a pale-yellow oil.

$^1$H NMR (CDCl$_3$) δ 1.34 (s, 6H), 1.95 (t, 2H, J=6.1 Hz), 2.23 (t, 1H, J=2.7 Hz), 3.04 (t, 2H, J=6.2 Hz), 3.53 (d, 2H, J=2.6 Hz), 7.05 (t, 1H, J=7.7 Hz), 7.32 (d, 1H, J=7.8 Hz), 7.38 (d, 1H, J=7.7 Hz).

(d) Methyl 2-hydroxy-4-[3-(4,4-dimethylthiochroman-8-yl) prop-1-ynyl]benzoate 670 mg (3.1 mmol) of 3-(4,4-dimethylthiochroman-8-yl) prop-1-yne, 860 mg (3.1 mmol) of methyl 2-hydroxy-4-4-iodobenzoate and 33 ml of triethylamine are introduced into a three-necked flask under argon. The reaction mixture is degassed by sparging with nitrogen, 174 mg (0.25 mmol) of bis(triphenylphosphine)-palladium(II) chloride and 71 mg of copper iodide are introduced and the reaction mixture is stirred at room temperature for eight hours. The reaction mixture is evaporated to dryness, the residue is taken up in ethyl acetate and hydrochloric acid (1N) and the organic phase is separated by settling, dried over magnesium sulphate and evaporated. The residue is purified by chromatography on a silica column eluted with a mixture composed of 99% heptane and 1% ethyl acetate. After evaporating the solvents, 1.50 g (75%) of methyl 2-hydroxy-4-[3-(4,4-dimethylthiochroman-8-yl)prop-1-ynyl]benzoate are collected in the form of a yellow oil.

$^1$H NMR (CDCl$_3$) δ 1.35 (s, 6H), 1.97 (t, 2H, J=6.0 Hz), 3.06 (t, 2H, J=6.1 Hz), 3.76 (s, 2H), 3.94 (s, 3H), 6.96 (dd, 1H, J=8.2/1.5 Hz), 7.04 to 7.10 (m, 2H), 7.33 (d, 1H, J=6.9 Hz), 7.41 (d, 1H, J=7.4 Hz), 7.75 (d, 1H, J=8.2 Hz).

EXAMPLE 6

2-Hydroxy-4-[3-(4,4-dimethylthiochroman-8-yl) prop-1-ynyl]benzoic Acid

In a way analogous to Example 2, from 1.40 g (3.8 mmol) of the compound obtained in Example 5(d), 960 mg (70%) of 2-hydroxy-4-[3-(4,4-dimethylthiochroman-8-yl)prop-1-ynyl]benzoic acid are obtained in the form of a white solid with a melting point of 190–191° C.

$^1$H NMR (d$_6$-DMSO) δ 1.29 (s, 6H), 1.69 (t, 2H, J=5.9 Hz), 3.04 (t, 2H, J=6.0 Hz), 3.75 (s, 2H), 6.96 to 6.99 (m, 2H), 7.06 (t, 1H, J=7.7 Hz), 7.32 (d, 1H, J=7.3 Hz), 7.38 (d, 1H, J=7.8 Hz), 7.76 (d, 1H, J=8.4 Hz).

EXAMPLE 7

Ethyl 4-[3-hydroxy-3-(5,5,8,8-tetramethyl-3-phenyl-5,6,7,8-tetrahydronaphth-1-yl)prop-1-ynyl]benzoate (a) 3-bromo-5,5,8,8-tetramethyl-5,6,7,8-tetrahydronaphth1-ol 13.40 g (100.0 mmol) of ammonium chloride and 100 ml of dichloromethane are introduced into a three-necked flask under an argon atmosphere. A solution composed of 34.60 g (199.0 mmol) of 3-bromophenol, 89.00 g (486.0 mmol) of 2,5-dichloro-2,5-dimethylhexane and 300 ml of dichloromethane is added dropwise. The reaction mixture is stirred for sixteen hours at room temperature. The reaction mixture is poured into water and extracted with dichloromethane, the extract is washed with water and the organic phase is separated by settling, dried over magnesium sulphate and evaporated. The residue obtained is purified by chromatography on a silica column eluted with a mixture composed of 80% heptane and 20% dichloromethane. After evaporating the solvents, 30.00 g (53%) of the expected compound are collected in the form of white crystals with a melting point of 93° C.

$^1$H NMR (CDCl$_3$) δ 1.25 (s, 6H), 1.38 (s, 6H), 1.57 to 1.69 (m, 4H), 4.78 (s, 1H), 6.64 (d, 1H, J=2.0 Hz), 7.04 (d, 1H, J=2.0 Hz).

(b) 5,5,8,8-tetramethyl-3-phenyl-5,6,7,8-tetrahydronaphth-1-ol 12.93 g (106.0 mmol) of phenylboronic acid, 20.00 g (70.7 mmol) of the compound obtained in Example 7(a), 400 ml of DME and 70 ml of an aqueous potassium carbonate solution (2M) are introduced into a three-necked flask. The reaction mixture is degassed by sparging with argon, 4.08 g (3.5 mmol) of tetrakistriphenylphosphinepalladium(O) are added and the reaction mixture is heated to 90° C. for eight hours. The reaction mixture is poured into water and extracted with ethyl acetate and the organic phase is separated by settling, dried over magnesium sulphate and evaporated. The residue obtained is purified by chromatography on a silica column eluted with heptane. After evaporating the solvents, 13.44 g (68%) of the expected compound are collected in the form of a white powder with a melting point of 121° C.

$^1$H NMR (CDCl$_3$) δ 1.33 (s, 6H), 1.46 (s, 6H), 1.65 to 1.73 (m, 4H), 4.77 (s, 1H), 6.69 (d, 1H, J=1.8 Hz), 7.16 (d, 1H, J=1.8 Hz), 7.24 to 7.52 (m, 3H), 7.53 (d, 2H, J=8.5 Hz).

(c) 5,5,8,8-tetramethyl-3-phenyl-5,6,7,8-tetrahydronaphth-1-yl trifluoromethanesulphonate 13.44 g (47.9 mmol) of the compound obtained in Example 7(b), 100 ml of dichloromethane and 9.95 g (81.5 mmol) of N,N-dimethyl-4-aminopyridine are introduced into a three-necked flask under argon. The mixture is cooled to 0° C. and 12.1 ml (71.9 mmol) of triflic anhydride are added dropwise. The temperature is returned naturally to room temperature over sixteen hours and the reaction mixture is evaporated to dryness. Ethyl acetate is added and the mixture is acidified to pH 3 with 1N hydrochloric acid. The product is extracted with ethyl acetate, the organic phase is washed with water and then using a saturated sodium chloride solution, dried over magnesium sulphate and filtered, and the solvents are evaporated 19.29 g (97%) of the expected compound are obtained in the form of a white powder with a melting point of 110° C.

$^1$H NMR (CDCl$_3$) δ 1.35 (s, 6H), 1.45 (s, 6H), 1.71 (s, 4H), 7.35 to 7.55 (m, 7H).

(d) Methyl 5,5,8,8-tetramethyl-3-phenyl-5,6,7,8-tetrahydrophthalene-1-carboxylate 16.12 g (39.1 mmol) of the triflate obtained in Example 7(c), 1.61 g (3.9 mmol) of 1,3-bis(diphenyl-phosphino) propane (DPPP), 440 mg (1.9 mmol) of palladium acetate, 130 ml of DMF, 10.9 ml (78.2 mmol) of triethylamine and 17.1 ml (390.8 mmol) of methanol are introduced into a hydrogenation device. The reaction mixture is enclosed under a pressure of 4 bar of carbon monoxide and heated with stirring at 70° C. for seven hours The mixture is cooled and evaporated as far as possible, the residue is taken up in a saturated sodium chloride solution and extracted with ethyl acetate, and the organic phase is washed using a dilute hydrochloric acid solution and then with water, dried over magnesium sulphate and evaporated. The residue obtained is purified by chromatography on a silica column eluted with heptane. After evaporating the solvents, 7.60 g (60%) of the expected compound are collected in the form of a white powder with a melting point of 118° C.

$^1$H NMR (CDCl$_3$) δ 1.35 (s, 6H), 1.40 (s, 6H), 1.65 to 1.69 (m, 2H), 1.76 to 1.80 (m, 2H), 3.91 (s, 3H), 7.30 (d, 1H, J=2.0 Hz), 7.34 to 7.46 (m, 3H), 7.59 (d, 2H, J=7.0 Hz), 7.61 (d, 1H, J=2.0 Hz).

(e) (5,5,8,8-tetramethyl-3-phenyl-5,6,7,8-tetrahydronaphth-1-yl)-methanol 80 ml of ethyl ether and 2.68 g (70.7 mmol) of lithium aluminium hydride are introduced into a 1 l three-necked flask. The reaction mixture is cooled to 0° C. and then 7.60 g (23.5 mmol) of the compound obtained in Example 7(d), in solution in 80 ml of ethyl ether, are introduced dropwise. The reaction mixture is stirred for sixteen hours at room temperature, then a saturated sodium chloride solution is added dropwise, the mixture is filtered through Celite, and water and ethyl ether are added. The product is extracted with ethyl ether, the organic phase is washed with water to neutral pH, dried over magnesium sulphate and filtered, and the solvents are evaporated. 6.82 g (98%) of the expected compound are collected in the form of white crystals with a melting point of 80–82° C.

$^1$H NMR (CDCl$_3$) δ 1.36 (s, 6H), 1.45 (s, 6H), 1.61 (t, 1H, J=5.8 Hz), 1.71 (s, 4H), 4.95 (d, 2H, J=5.7 Hz), 7.30 to 7.35

(m, 1H), 7.43 (t, 2H, J=7.7 Hz), 7.53 (d, 1H, J=2.1 Hz), 7.58 to 7.61 (m, 3H).

(f) 5,5,8,8-tetramethyl-3-phenyl-5,6,7,8-tetrahydronaphthalene-1-carbaldehyde 6.560 g (22.2 mmol) of the compound obtained in Example 7(e), 38.73 g (445.6 mmol) of manganese oxide and 500 ml of dichloromethane are mixed in a one liter round-bottomed flask. The reaction mixture is stirred for twenty hours at room temperature and then the manganese oxide is filtered off and washed with dichloromethane. After evaporating the solvents, 4.44 g (68%) of the expected compound are collected in the form of a yellow powder with a melting point of 113° C.

$^1$H NMR (CDCl$_3$) δ 1.37 (s, 6H), 1.57 (s, 6H), 1.75 (s, 4H), 7.33 to 7.48 (m, 3H), 7.58 to 7.62 (m, 2H), 7.77 (d, 1H, J=2.2 Hz), 7.95 (d, 1H, J=2.2 Hz).

(g) 1-(5,5,8,8-tetramethyl-3-phenyl-5,6,7,8-tetrahydronaphth-1-yl)-3-(trimethylsilanyl)-prop-2-yn-1-ol 2.43 ml (17.2 mmol) of trimethylsilylacetylene and 25 ml of THF are introduced into a three-necked flask. A solution composed of 6.89 ml (17.2 mmol) of n-butyllithium (2.5M in hexane) is added dropwise at −78° C. under a stream of nitrogen and the reaction mixture is allowed to return to room temperature. This solution is introduced dropwise into a cold (−78° C.) solution composed of 4.20 g (14.4 mmol) of the compound obtained in Example 7(f) and of 25 ml of THF. The reaction mixture is allowed to return to room temperature, poured onto an aqueous ammonium chloride solution and extracted with ethyl ether and the organic phase is separated by settling, dried over magnesium sulphate and evaporated. 5.060 g (100%) of the expected compound are obtained in the form of a white powder with a melting point of 145° C.

$^1$H NMR (CDCl$_3$) δ 1.34 (s, 3H), 1.36 (s, 3H), 1.48 (s, 3H), 1.51 (s, 3H) 1.66 to 1.76 (m, 4H), 2.19 (br s, 1H), 6.13 (s, 1H) 7.30 to 7.36 (m, 1H), 7.41 to 7.47 (m, 2H), 7.55 (d, 1H, J=2.0 Hz), 7.60 (d, 2H, J=7.1 Hz), 7.90 (d 1H, J=2.1 Hz).

(h) 1-(5,5,8,8-tetramethyl-3-phenyl-5,6,7,8-tetrahydronaphth-1-yl)prop-2-yn-1-ol 5.60 g (14.3 mmol) of the compound obtained in Example 7(g) are mixed with 30 ml of THF in a 500 ml three-necked flask and 15.8 ml (17.4 mmol) of a tetrabutylammonium fluoride solution (1.1M in THF) are added dropwise. The reaction mixture is stirred at room temperature for one hour, poured into water and extracted with ethyl ether and the organic phase is separated by settling, dried over magnesium sulphate and evaporated. 4.07 g (89%) of the expected compound are collected in the form of a yellow oil.

$^1$H NMR (CDCl$_3$) δ 1.34 (s, 3H), 1.35 (s, 3H), 1.48 (s, 3H), 1.52 (s, 3H), 1.66 to 1.75 (m, 4H), 2.30 (br s, 1H), 2.59 (d, 1H, J=2.1 Hz), 6.16 (d, 1H, J=2.0 Hz), 7.31 to 7.37 (m, 1H), 7.41 to 7.47 (m, 2H), 7.55 (d, 1H, J=2.1 Hz), 7.60 (d, 2H, J=7.1 Hz), 7.88 (d, 1H, J=2.1 Hz).

(i) ethyl 4-[3-hydroxy-3-(5,5,8,8-tetramethyl-3-phenyl-5,6,7,8-tetrahydronaphth-1-yl)prop-1-ynyl]benzoate In a way analogous to Example 3(c), by reaction of 4.07 g (12.8 mmol) of the compound obtained in Example 7(h) with 3.53 g (12.8 mmol) of ethyl 4-iodobenzoate, 4.57 g (77%) of ethyl 4-[3-hydroxy-3-(5,5,8,8-tetramethyl-3-phenyl-5,6,7,8-tetrahydronaphth-1-yl)prop-1-ynyl]benzoate are obtained in the form of an orange powder with a melting point of 121° C.

$^1$H NMR (CDCl$_3$) δ 1.35 (s, 3H), 1.35 (t, 3H, J=7.1 Hz), 1.37 (s, 3H), 1.53 (s, 3H), 1.56 (s, 3H), 1.67 to 1.80 (m, 4H), 2.45 (d, 1H, J=4.9 Hz), 4.35 (q, 2H, J=7.1 Hz), 6.40 (d, 1H, J=4.9 Hz), 7.30 to 7.36 (m, 1H), 7.41 to 7.49 (m, 4H), 7.57 (d, 1H, J=2.0 Hz), 7.61 (d, 2H, J=7.1 Hz), 7.95 (d, 1H, J=2.0 Hz), 7.96 (d, 2H, J=6.0 Hz).

EXAMPLE 8

4-[3-Hydroxy-3-(5,5,8,8-tetramethyl-3-phenyl-5,6,7,8-tetrahydronaphth-1-yl)prop-1-ynyl]benzoic Acid In a way analogous to Example 2, from 3.60 g (7.7 mmol) of the compound obtained in Example 7(i), 3.32 g (98%) of 4-[3-hydroxy-3-(5,5,8,8-tetramethyl-3-phenyl-5,6,7,8-tetrahydronaphth-1-yl)prop-1-ynyl]benzoic acid are obtained in the form of an orangey-beige powder with a melting point of 250° C.

$^1$H NMR (d$_6$-DMSO) δ 1.12 (s, 3H), 1.13 (s, 3H), 1.26 (s, 3H), 1.27 (s, 3H), 1.43 to 1.55 (m, 4H), 5.97 (br s, 1H), 7.13 to 7.19 (m, 1H), 7.25 to 7.33 (m, 4H), 7.36 (d, 1H, J=1.9 Hz), 7.45 (d, 2H, J=7.3 Hz), 7.68 (d, 1H, J=2.0 Hz), 7.70 (d, 2H, J=8.4 Hz), 12.92 (br s, 1H).

EXAMPLE 9

4-[3-(5,5,8,8-Tetramethyl-3-phenyl-5,6,7,8-tetrahydronaphth-1-yl)prop-1-ynyl]benzoic Acid 2.00 g (4.6 mmol) of the compound obtained in Example 8, 1.45 ml (9.1 mmol) of triethylsilane, 30 ml of dichloromethane and 3.5 ml of trifluoroacetic acid are introduced into a one liter round-bottomed flask under a nitrogen atmosphere. The reaction mixture is stirred for two hours at room temperature and hydrolysed using a 1N HCl solution, and the product is extracted with ethyl ether. The organic phase is washed with water and dried over magnesium sulphate and the solvent is evaporated to dryness. The residue obtained is purified by chromatography on a silica column eluted with a mixture composed of 50% ethyl acetate and 50% heptane. After evaporating the solvents, 370 mg (19%) of 4-[3-(5,5,8,8-tetramethyl-3-phenyl-5,6,7,8-tetrahydronaphth-1-yl)prop-1-ynyl]benzoic acid are collected in the form of a white powder with a melting point of 228° C.

$^1$H NMR (d$_6$-DMSO) δ 1.22 (s, 6H), 1.35 (s, 6H), 4.00 (s, 2H), 7.24 to 7.27 (m, 2H), 7.33 to 7.41 (m, 4H), 7.46 (s, 1H), 7.53 (d, 2H, J=7.3 Hz), 7.78 (d, 2H, J=8.2 Hz).

EXAMPLE 10

Ethyl 4-[3-(4,4-dimethylthiochroman-5-yl)-3-hydroxy-prop-1-ynyl]benzoate (a) 1-methoxy-3-(3-methylbut-2-enylsulphanyl)benzene 50.45 g (360.0 mmol) of 3-methoxythiophenol, 360 ml of acetone and 14.40 g (360.0 mmol) of sodium hydroxide pellets are introduced into a one liter round-bottomed flask under a nitrogen atmosphere and the mixture is heated at reflux for three hours. A solution composed of 53.6 g (360.0 mmol) of 2-methyl-4-bromo-2-butene and of 60 ml of acetone is added dropwise. Reflux is maintained for sixteen hours and the reaction mixture is evaporated to dryness. Water is added, extraction is carried out with ethyl acetate, the organic phase is washed with water and then using a saturated sodium chloride solution, dried over magnesium sulphate and filtered, and the solvents are evaporated. The residue obtained is distilled under reduced pressure (5×10$^{-2}$ bar/113° C.) to produce 67.81 g (90%) of the expected compound in the form or a pale-yellow oil.

$^1$H NMR (CDCl$_3$) δ 1.62 (s, 3H), 1.72 (s, 3H), 3.55 (d, 2H, J=7.7 Hz), 3.79 (s, 3H), 5.31 (tt, 1H, J=7.7/1.3 Hz), 6.71 (dt, 1H, J=8.3/1.8 Hz), 6.87 to 6.92 (m, 2H), 7.18 (t, 1H, J=7.9 Hz).

(b) 5-methoxy-4,4-dimethylthiochroman 62.00 g (298.0 mmol) of the compound obtained in Example 10(a), 85.00 g (446.0 mmol) of paratoluenesulphonic acid and 500 ml of toluene are introduced into a round-bottomed flask. The mixture is heated at reflux for two hours, cooled, water and ethyl acetate are then added and extraction is carried out with ethyl acetate. The organic phase is separated by settling, washed with water and then using a saturated sodium chloride solution and dried over magnesium sulphate, and the solvents are evaporated. 65.19 g of a yellow oil are obtained, which oil is distilled under reduced pressure ($5 \times 10^{-2}$ bar/120–122° C.) to produce 17.40 g (28%) of the expected compound in the form of a colourless oil.

$^1$H NMR (CDCl$_3$) δ 1.41 (s, 3H), 2.00 to 2.05 (m, 2H), 2.86 to 2.90 (m, 2H), 3.80 (s, 3H), 6.58 (d, 1H, J=8.1 Hz), 6.72 (dd, 1H, J=7.9/1.2 Hz), 6.98 (t, 1H, J=8.0 Hz).

(c) 4,4-dimethylthiochroman-5-ol 17.40 g (83.5 mmol) of the compound obtained in Example 10(b), 28.10 g (333.0 mmol) of sodium ethanethiolate and 100 ml of DMF are introduced into a round-bottomed flask. The mixture is heated at 150° C. for two hours and then stirred for sixteen hours at room temperature, poured onto a 1N HCl/ethyl ether mixture and extracted with ethyl ether. The organic phase is separated by settling, dried over magnesium sulphate and evaporated. The residue obtained is purified by chromatography on a silica column eluted with a mixture composed of 20% ethyl acetate and of 80% heptane. 14.07 g (87%) of the expected compound are collected in the form of a light-yellow solid with a melting point of 48° C.

$^1$H NMR (CDCl$_3$) δ 1.45 (s, 3H), 2.01 to 2.07 (m, 2H), 2.86 to 2.91 (m, 2H), 5.00 (s, 1H), 6.34 (dd, 1H, J=7.8/1.3 Hz), 6.69 (dd, 1H, J=7.9/1.2 Hz), 6.84 (d, 1H, J=7.8 Hz).

(d) 4,4-dimethylthiochroman-5-yl Trifluoromethanesulphonate 13.63 g (70.1 mmol) of 4,4-dimethylthiochroman-5-ol obtained in Example 10(c), 11.14 g (91.2 mmol) of N,N-dimethylaminopyridine and 100 ml of dichloromethane are introduced into a 500 ml round-bottomed flasks under a stream of nitrogen. The mixture is cooled to 0° C. and 14.16 ml (84.2 mmol) of triflic anhydride are added dropwise. The reaction mixture is stirred for 30 minutes at room temperature and then a 1N HCl solution and dichloromethane are added. The product is extracted with dichloromethane and the organic phase is washed with water to neutral pH, dried over magnesium sulphate and filtered. The reside obtained is purified by chromatography on a silica column eluted with a mixture composed of 90% heptane and 10% ethyl acetate. After evaporating the solvents, 16.32 g (71%) of the expected compound are collected in the form of a yellow oil.

$^1$H NMR (CDCl$_3$) δ 1.46 (s, 3H), 2.01 to 2.06 (m, 2H), 2.93 to 2.98 (m, 2H), 7.00 to 7.12 (m, 3H).

(e) Methyl 4,4-dimethylthiochroman-5-carboxylate

In a way analogous to Example 7(d), from 14.23 g (43.6 mmol) of the compound obtained in Example 10(d), 8.81 g (85%) of the expected compound are obtained in the form of a yellow oil.

$^1$H NMR (CDCl$_3$) δ 1.39 (s, 3H), 1.91 (t, 2H, J=6.1 Hz), 3.05 (t, 2H, J=6.1 Hz), 3.89 (s, 3H), 6.96 (dd, 1H, J=7.4/1.8 Hz), 7.03 (t, 1H, J=7.4 Hz), 7.16 (dd, 1H, J=7.5/1.8 Hz).

(f) 4,4-dimethylthiochroman-5-methanol 8.81 g (37.3 mmol) of the ester obtained in Example 10(e) and 300 ml of toluene are mixed in a 500 ml round-bottomed flask. After cooling to −78° C., a diisobutylaluminium hydride solution (1M in toluene) is run in dropwise while maintaining this temperature of −78° C. The reaction mixture is stirred for one hour at this temperature, an aqueous magnesium sulphate paste is then added, the mixture is stirred and is extracted with ethyl ether. The organic phase is dried over magnesium sulphate and filtered, and the solvents are evaporate. The residue obtained is purified by chromatography on a silica column eluted with a mixture composed of 70% heptane and 30% ethyl acetate. After evaporating the solvents, 4.37 g (56%) of the expected compound are collected in the form of a light yellow powder with a melting point of 53° C.

$^1$H NMR (CDCl$_3$) δ 1.45 (s, 6H), 2.04 (t, 2H, J=6.4 Hz), 2.95 (t, 2H, J=6.4 Hz), 4.87 (d, 2H, J=5.8 Hz), 7.01 to 7.08 (m, 2H), 7.17 to 7.22 (m, 1H).

(g) 4,4-dimethylthiochroman-5-carbaldehyde 4.37 g (21.0 mmol) of the alcohol obtained in Example 10(f), 36.47 g (419.5 mmol) of manganese oxide and 300 ml of dichloromethane are mixed in a 500 ml round-bottomed flask. The reaction mixture is stirred for twenty hours at room temperature, the manganese oxide is then filtered off through Celite and the dichloromethane is evaporated. After evaporating the solvents, 3.25 g (75%) of the expected compound are collected in the form of a yellow oil.

$^1$H NMR (CDCl$_3$) δ 1.54 (s, 6H), 2.03 (t, 2H, J=5.9 Hz), 3.01 (t, 2H, J=6.0 Hz), 7.15 (d, 1H, J=7.6 Hz), 7.25 to 7.29 (m, 1H), 7.49 (dd, 1H, J=7.4/1.4 Hz), 10.73 (s, 1H).

(h) 1-(4,4-dimethylthiochroman-5-yl)-3-(trimethylsilanyl)prop-2-yn-1-ol

In a way analogous to Example 7(g), from 3.25 g (15.7 mmol) of the compound obtained in Example 10(g), 4.79 g (100%) of 1-(4,4-dimethylthiochroman-5-yl)-3-(trimethylsilanyl)prop-2-yn-1-ol are obtained in the form of a yellow oil.

$^1$H NMR (CDCl$_3$) δ 0.16 (s, 9H), 1.48 (s, 3H), 1.50 (s, 3H), 2.04 to 2.09 (m, 2H), 2.14 (d, 1H, J=5.2 Hz), 2.87 to 2.93 (m, 2H), 6.04 (d, 1H, J=5.1 Hz), 7.05 to 7.13 (m, 2H) 7.50 to 7.54 (q, 1H, J=3.1 Hz).

(i) 1-(4,4-dimethylthiochroman-5-yl)prop-2-yn-1-ol

In a way analogous to Example 7(h), from 4.79 g (15.7 mmol) of the compound obtained in Example 10(h), 3.34 g (89%) of 1-(4,4-dimethylthiochroman-5-yl)prop-2-yn-1-ol are obtained in the form of beige crystals with a melting point of 88° C.

$^1$H NMR (CDCl$_3$) δ 1.49 (s, 3H), 1.51 (s, 3H), 2.04 to 2.10 (m, 2H), 2.26 (d, 1H, J=5.1 Hz), 2.59 (d, 1H, J=2.2 Hz), 2.88 to 2.94 (m, 2H), 6.07 (br s, 1H), 7.07 to 7.14 (m, 2H), 7.52 to 7.55 (q, 1H, J=3.0 Hz).

(j) Ethyl 4-[3-(4,4-dimethylthiochroman-5-yl)-3-hydroxyprop-1-ynyl]benzoate

In a way analogous to Example 3(c), by reaction of 3.34 g (14.4 mmol) of the compound obtained in Example 10(i) with 3.97 g (14.4 mmol) of ethyl 4-iodobenzoate, 4.66 g (35%) of ethyl 4-[3-(4,4-dimethylthiochroman-5-yl)-3-hydroxyprop-1-ynyl]benzoate are obtained in the form of an orangey powder with a melting point of 108° C.

$^1$H NMR (CDCl$_3$) δ 1.39 (t, 3H, J=7.1 Hz), 1.54 (s, 3H), 1.56 (s, 3H), 2.08 to 2.13 (m, 2H), 2.28 (d, 1H, J=5.3 Hz), 2.90 to 2.96 (m, 2H), 4.37 (q, 2H, J=7.1 Hz), 6.31 (d, 1H, J=5.3 Hz), 7.09 to 7.17 (m, 2H), 7.48 (d, 2H, J=8.3 Hz), 7.60 (dd, 1H, J=6.4/2.8 Hz), 7.98 (d, 2H, J=8.4 Hz).

EXAMPLE 11

4-[3-(4,4-Dimethylthiochroman-5-yl)-3-hydroxyprop-1-ynyl]benzoic Acid

In a way analogous to Example 2, from 4.66 g (12.3 mmol) of the compound obtained in Example 10(j), 3.41 g (78%) of 4-[3-(4,4-dimethylthiochroman-5-yl)-3- hydroxyprop-1-ynyl]benzoic acid are obtained in the form of a brown solid with a melting point of 198° C.

$^1$H NMR (CDCl$_3$) δ 1.54 (s, 3H), 1.56 (s, 3H), 2.08 to 2.12 (m, 2H), 2.90 to 2.94 (m, 2H), 6.29 (s, 1H), 7.10 to 7.16 (m, 2H), 7.43 (d, 2H, J=8.2 Hz), 7.61 (dd, 1H, J=6.7/2.3 Hz), 7.99 (d, 2H, J=8.3 Hz).

EXAMPLE 12

4-[3-(4,4-Dimethylthiochroman-5-yl)prop-1-ynyl] benzoic Acid

In a way analogous to Example 9, from 2.06 g (5.82 mmol) of the compound obtained in Example 11, 1.00 g (51%) of 4-[3-(4,4-dimethylthiochroman-5-yl)-prop-1-ynyl] benzoic acid is obtained in the form of beige crystals with a melting point of 207° C.

1H NMR (d$_6$-DMSO) δ 1.51 (s, 6H), 2.05 to 2.10 (m, 2H), 2.92 to 2.97 (m, 2H), 4.01 (s, 2H), 7.01 to 7.03 (m, 2H), 7.25 to 7.31 (m, 1H), 7.45 (d, 2H, J=8.3 Hz), 7.97 (d, 2H, J=8.3 Hz).

EXAMPLE 13

Ethyl 4-[3-(3,5-di-tert-butyl-2-(methoxymethoxy)-phenyl)-3-hydroxyprop-1-ynyl]benzoate (a) 1-bromo-3,5-di-tert-butyl-2-(methoxymethoxy)-benzene 40.00 g (140.2 mmol) of 2,4-di-tert-butyl-6-bromophenol and 400 ml of DMF are introduced into a one liter three-necked flask. The solution obtained is cooled to 5–10° C., 4.70 g of sodium hydride are added and the mixture is stirred at 10° C. for 30 minutes. 11.7 ml (154.0 mmol) of chloromethyl methyl ether are then added dropwise and the reaction mixture is stirred for one hour at room temperature. The reaction mixture is poured into a 1N HCl/ethyl ether mixture and extracted with ethyl ether and the organic phase is separated by settling, dried over magnesium sulphate and evaporated. 46.00 g (130%) of the expected compound are collected in the form of an orange oil.

$^1$H NMR (CDCl$_3$) δ 1.28 (s, 9H), 1.43 (s, 9H), 3.69 (s, 3H), 5.21 (s, 2H), 7.30 (d, 1H, J=2.4 Hz), 7.39 (d, 1H, J=2.4 Hz).

(b) 3,5-di-tert-butyl-2-(methoxymethoxy)benzaldehyde 46.00 g (140.0 mmol) of the compound obtained in Example 13 (a) and 500 ml of THF are introduced into a three-necked flask under a stream of nitrogen. 61.5 ml (154.00 mmol) of an n-butyllithium solution (2.5M in hexane) are added dropwise at −78° C. and the mixture is stirred for 30 minutes at this same temperature. 13.0 ml (168.0 mmol) of DMF are then added dropwise and the mixture is allowed to return to room temperature. The reaction mixture is acidified with hydrochloric acid (1N) and extracted with ethyl ether and the organic phase is separated by settling, dried over magnesium sulphate and evaporated. 46.00 g (100%) of the expected compound are collected in the form of an orange oil.

$^1$H NMR (CDCl$_3$) δ 1.32 (s, 9H), 1.44 (s, 9H), 3.64 (s, 3H), 5.02 (s, 2H), 7.64 (d, 1H, J=2.6 Hz), 7.72 (d, 1H, J=2.6 Hz), 10.22 (s, 1H).

(c) 1-(3,5-di-tert-butyl-2-(methoxymethoxy)phenyl)-3-(trimethylsilanyl)prop-2-yn-1-ol 18.60 g (190.0 mmol) of trimethylsilylacetylene and 190 ml of THF are introduced into a three-necked flask under a stream of nitrogen and the solution thus obtained is cooled to −78° C. 76.0 ml (190.0 mmol) of an n-butyllithium solution (2.5M in hexane) are added dropwise at −70° C., the reaction mixture is stirred for 30 minutes at this same temperature and is returned to −20° C. This solution is run dropwise onto a cold (−70° C.) solution composed of 44.00 g (158.0 mmol) of the compound obtained in Example 13(b) in solution in 550 ml or anhydrous THF. The temperature of the reaction mixture is returned to room temperature over two hours, the reaction mixture is then acidified with hydrochloric acid (1N) and extracted with ethyl ether and the organic phase is separated by settling, dried over magnesium sulphate and evaporated. 59.00 g (100%) of the expected compound are collected in the form of an orange oil.

$^1$H NMR (CDCl$_3$) δ 1.12 (s, 9H), 1.18 (s, 9H), 3.49 (s, 3H), 3.81 (d, 1H, J=5.4 Hz), 4.68 (d, 1H, J=6.3 Hz), 4.88 (d, 1H, J=6.3 Hz), 5.55 (d, 1H, J=5.3 Hz), 7.16 (d, 1H, J=2.5 Hz), 7.56 (d, 1H, J=2.5 Hz).

(d) 1-(3,5-di-tert-butyl-2-(methoxymethoxy)phenyl)-prop-2-yn-1-ol 58.00 g (154.0 mmol) of the compound obtained in Example 13(c) and 300 ml of THF are introduced into a three-necked flask under a stream of nitrogen and a tetrabutylammonium fluoride solution (1M in THF) is run in dropwise. The reaction mixture is stirred for two hours at room temperature, is then acidified with hydrochloric acid (1N) and extracted with ethyl ether and the organic phase is separated by settling, dried over magnesium sulphate and evaporated. 6. [lacuna] g (13%) of the expected compound are collected in the form of an orange oil and 12.00 g (30%) of 1-(3,5-di-tert-butyl-2-hydroxyphenyl)prop-2-yn-1-ol are collected in the form of an orange oil.

$^1$H NMR of the expected compound (CDCl$_3$) δ 1.32 (s, 9H), 1.39 (s, 9H), 2.61 (d, 1H, J=2.2 Hz), 3.70 (s, 3H), 3.90 (d, 1H, J=5.5 Hz), 4.90 (d, 1H, J=6.3 Hz), 5.08 (d, 1H, J=6.2 Hz), 5.79 (dd, 1H, J=5.4/2.3 Hz), 7.37 (d, 1H, J=2.5 Hz), 7.70 (d, 1H, J=2.5 Hz).

$^1$H NMR of 1-(3,5-di-tert-butyl-2-hydroxyphenyl)prop-2-yn-1-ol (CDCl$_3$) δ 1.30 (s, 9H), 1.43 (s, 9H), 2.72 (br s, 1H), 2.80 (d, 1H, J=2.3 Hz), 4.94 to 5.05 (m, 1H), 5.66 (br s, 1H), 7.27 (d, 1H, J=2.3 Hz), 7.32 (d, 1H, J=2.4 Hz).

(e) Ethyl 4-[3-(3,5-di-tert-butyl-2-(methoxymethoxy)-phenyl)-3-hydroxyprop-1-ynyl] benzoate 6.00 g (19.7 mmol) of the compound obtained in Example 13(d), 5.40 g (19.7 mmol) of ethyl 4-iodobenzoate and 40 ml of triethylamine are introduced successively into a round-bottomed flask. The reaction mixture is degassed with nitrogen for 20 minutes and then 375 mg of CuI and 700 mg of bis(triphenylphosphine)palladium(II) chloride are added. The reaction mixture is stirred at room temperature for five hours, poured into water, acidified with 1N hydrochloric acid and extracted with ethyl ether and the organic phase is separated by settling, dried over magnesium sulphate and evaporated. The residue obtained is purified by chromatography on a silica column eluted with a mixture composed of 10% ethyl acetate and of 90% heptane. After evaporating the solvents, 6.00 g (69%) of ethyl 4-[3-(3,5-di-tert-butyl-2-(methoxymethoxy)-phenyl)-3-hydroxyprop-1-ynyl] benzoate are collected in the form of an orangey powder with a melting point of 89–91° C.

$^1$H NMR (CDCl$_3$) δ 1.34 (s, 9H), 1.39 (t, 3H, J=7.1 Hz), 1.41 (s, 9H), 3.73 (s, 3H), 4.09 (d, 1H, J=5.5 Hz), 4.37 (q, 2H, J=7.1 Hz), 4.93 (d, 1H, J=6.3 Hz), 5.12 (d, 1H, J=6.3 Hz), 6.00 (d, 1H, J=5.5 Hz), 7.40 (d, 1H, J=2.5 Hz), 7.53 (d, 2H, J=8.4 Hz), 7.79 (d, 1H, J=2.5 Hz), 7.99 (d, 2H, J=8.4 Hz).

EXAMPLE 14

4-[3-(3,5-Di-tert-butyl-2-(methoxymethoxy)phenyl)-3-hydroxyprop-1-ynyl]benzoic Acid In a way analogous to Example 2, from 1.50 g (3.3 mmol) of the compound obtained in Example 13(e), 1.20 g (85%)

of 4-[3-(3,5-di-tert-butyl-2-(methoxymethoxy)phenyl)-3-hydroxyprop-1-ynyl]benzoic acid are obtained in the form of a beige powder with a melting point of 197° C.

$^1$H NMR (CDCl$_3$) δ 1.33 (s, 9H), 1.41 (s, 9H), 3.73 (s, 3H), 4.35 (br s, 1H), 4.97 (d, 1H, J=6.1 Hz), 5.12 (d, 1H, J=6.1 Hz), 6.00 (s, 1H), 7.38 (d, 1H, J=2.5 Hz), 7.51 (d, 2H, J=8.4 Hz), 7.78 (d, 1H, J=2.5 Hz), 8.00 (d, 2H, J=8.4 Hz).

EXAMPLE 15

Ethyl 4-[3-(3,5-di-tert-butyl-2-hydroxyphenyl)-3-hydroxyprop-1-ynyl]benzoate

In a way analogous to Example 13(e), by reaction of 10.00 g (38.4 mmol) of 1-(3,5-di-tert-butyl-2-hydroxyphenyl)prop-2-yn-1-ol obtained in Example 13(d) with 10.60 g (38.4 mmol) of ethyl 4-iodo-benzoate, 5.00 g (32%) of ethyl 4-[3-(3,5-di-tert-butyl-2-hydroxyphenyl)-3-hydroxyprop-1-ynyl]benzoate are obtained in the form of an off-white solid with a melting point of 142–144° C.

$^1$H NMR (CDCl$_3$) δ 1.31 (s, 9H), 1.39 (t, 3H, J=7.1 Hz), 1.44 (s, 9H), 2.80 (d, 1H, J=6.2 Hz), 4.37 (q, 2H, J=7.1 Hz), 5.90 (d, 1H, J=6.2 Hz), 7.34 (s, 2H), 7.37 (s, 1H), 7.53 (d, 2H, J=8.4 Hz), 8.02 (d, 2H, J=8.4 Hz).

EXAMPLE 16

Ethyl 4-[3-(3,5-di-tert-butyl-2-hydroxyphenyl)prop-1-ynyl]benzoate

In a way analogous to Example 9, from 3.00 g (7.3 mmol) of the compound obtained in Example 15, 1.30 g (45%) of ethyl 4-[3-(3,5-di-tert-butyl-2-hydroxyphenyl)prop-1-ynyl]benzoate are obtained in the form of a white powder with a melting point of 113–115° C.

$^1$H NMR (CDCl$_3$) δ 1.31 (s, 9H), 1.39 (t, 3H, J=7.1 Hz), 1.44 (s, 9H), 3.80 (s, 2H), 4.37 (q, 2H, J=7.1 Hz), 6.77 (br s, 1H), 7.13 (d, 1H, J=2.3 Hz), 7.27 (d, 1H, J=2.3 Hz), 7.48 (d, 2H, J=8.3 Hz), 7.98 (d, 2H, J=8,4 Hz).

EXAMPLE 17

Ethyl 4-[3-(3,5-di-tert-butyl-2-methoxyphenyl)-3-hydroxyprop-1-ynyl]benzoate (a) 1-bromo-3,5-di-tert-butyl-2-methoxybenzene In a way analogous to Example 13(a), from 25.00 g (87.6 mmol) of 2,4-di-tert-butyl-6-bromophenol and from 13.70 g (96.4 mmol) of methyl iodide, 27.00 g (100%) of 1-bromo-3,5-di-tert-butyl-2-methoxybenzene are obtained in the form of an orange oil.

$^1$H NMR (CDCl$_3$) δ 1.29 (s, 9H), 1.39 (s, 9H), 3.91 (s, 3H), 7.27 (d, 1H, J=2.4 Hz), 7.40 (d, 1H, J=2.4 Hz).

(b) 3,5-di-tert-butyl-2-methoxybenzaldehyde

In a way analogous to Example 13(b), from 25.00 g (83.5 mmol) of the compound obtained in Example 17(a), 21.00 g (100%) of the expected compound are obtained in the form of an orange oil.

$^1$H NMR (CDCl$_3$) δ 1.32 (S, 9H), 1.43 (s, 9H), 3.93 (s, 3H), 7.61 (d, 1H, J=2.6 Hz), 7.71 (d, 1H, J=2.5 Hz), 10.34 (s, 1H).

(c) 1-(3,5-di-tert-butyl-2-methoxyphenyl)-3-(trimethylsilanyl)prop-2-yn1-ol

In a way analogous to Example 13(c), from 21.00 g (85.0 mmol) of the compound obtained in Example 17(b), 30.00 g (100%) of the expected compound are obtained in the form of a beige powder with a melting point of 104–106° C., $^1$H NMR (CDCl$_3$) δ 1.13 (s, 9H), 1.20 (s, 9H), 2.39 (d, 1H, J=4.7 Hz), 3.69 (s, 3H), 5.59 (d, 1H, J=4.0 Hz), 7.15 (d, 1H, J=2.5 Hz), 7.43 (d, 1H, J=2.5 Hz).

(d) 1-(3,5-di-tert-butyl-2-methoxyphenyl)prop-2-yn-1-ol

In a way analogous to Example 13(d), from 23.00 g (66.0 mmol) of the compound obtained in Example 17(c), 25.00 g (100%) of the expected compound are obtained in the form of an orange oil.

$^1$H NMR (CDCl$_3$) δ 1.32 (s, 9H), 1.40 (s, 9H), 2.63 (d, 1H, J=2.2 Hz), 3.88 (s, 3H), 5.81 (d, 1H, J=2.2 Hz), 7.35 (d, 1H, J=2.5 Hz), 7.58 (d, 1H, J=2.5 Hz).

(e) Ethyl 4-[3-(3,5-di-tert-butyl-2-methoxyphenyl)-3-hydroxyprop-1-ynyl]benzoate In a way analogous to Example 13(e), by reaction of 23.30 g (85.0 mmol) of the compound obtained in Example 17(d) with 23.50 g (85.0 mmol) of ethyl 4-iodobenzoate, 20.00 g (55%) of ethyl 4-[3-(3,5-di-tert-butyl-2-methoxyphenyl)-3-hydroxyprop-1-ynyl]benzoate are obtained in the form of a grey powder with a melting point of 101–103° C.

$^1$H NMR (CDCl$_3$) δ 1.34 (s, 9H), 1.39 (t, 3H, J=5.2 Hz), 1.42 (s, 9H), 2.74 (d, 1H, J=5.4 Hz), 3.93 (s, 3H), 4.37 (q, 2H, J=7.1 Hz), 6.04 (d, 1H, J=5.4 Hz), 7.37 (d, 1H, J=2.5 Hz), 7.50 (d, 2H, J=8.4 Hz), 7.65 (d, 1H, J=2.5 Hz), 7.99 (d, 2H, J=8.4 Hz).

EXAMPLE 18

4-[3-(3,5-Di-tert-butyl-2-methoxyphenyl)-3-hydroxyprop-1-ynyl]benzoic Acid

In a way analogous to Example 2, from 5.00 g (11.8 mmol) of the compound obtained in Example 17(e), 4.50 g (96%) of 4-[3-(3,5-di-tert-butyl-2-methoxyphenyl)-3-hydroxyprop-1-ynyl]benzoic acid are obtained in the form of a light-yellow solid with a melting point of 208–209° C.

$^1$H NMR (CDCl$_3$) δ 1.29 (s, 9H), 1.37 (s, 9H), 3.83 (s, 3H), 5.80 (d, 1H, J=5.0 Hz), 6.19 (d, 1H, J=5.6 Hz), 7.27 (d, 1H, J=2.5 Hz), 7.53 (d, 2H, J=8.3 Hz), 7.62 (d, 1, J=2.4 Hz), 7.93 (d, 2H, J=8.3 Hz), 13.14 (br s, 1H).

EXAMPLE 19

4-[3-(3,5-Di-tert-butyl-2-methoxyphenyl)prop-1-ynyl]benzoic Acid

In a way analogous to Example 9, from 1.50 g (3.8 mmol) of the compound obtained in Example 18, 1.40 g (97%) of 4-[3-(3,5-di-tert-butyl-2-methoxyphenyl)prop-1-ynyl]benzoic acid are obtained in the form of a white powder with a melting point of 237–239° C.

$^1$H NMR (CDCl$_3$) δ 1.33 (s, 9H), 1.41 (s, 9H), 3.83 (s, 3H), 3.87 (s, 2H), 7.27 (d, 1H, J=2.2 Hz), 7.46 (d, 1H, J=2.2 Hz), 7.47 (d, 2H, J=8.2 Hz), 7.99 (d, 2H, J=8.2 Hz).

EXAMPLE 20

Ethyl 4-3-[5-tert-butyl-4-(methoxymethoxy)biphenyl-3-yl)-3-hydroxyprop-1-ynyl]benzoate (a) 2-tert-butyl-4-bromophenol 80.00 g (426.0 mmol) of 4-bromophenol and 8.00 g of Dowex 50WX8 sulphonic acid resin are mixed in a 250 ml three-necked flask. The mixture is heated to 80° C. and a stream of isobutylene is passed through for 30 hours. The reaction mixture is cooled and the residue is purified by passing through a silica column eluted with a mixture composed of 95% dichloromethane and of 5% heptane. 88.00 g (90%) of the expected compound are collected in the form of a yellow oil.

$^1$H NMR (CDCl$_3$) δ 1.38 (s, 9H), 4.79 (s, 1H), 6.55 (d, 1H, J=8.4 Hz), 7.16 (dd, 1H, J=8.4/2.4 Hz), 7.35 (d, 1H, J=2.4 Hz).

(b) 3-(tert-butyl)biphenyl-4-ol

In a way analogous to Example 7(b), by reaction of 40.00 g (175.0 mmol) of the compound obtained in Example 20(a) with 34.60 g (283.0 mmol) of phenylboronic acid, 27.00 g (68%) of the expected compound are obtained in the form of a brown oil.

$^1$H NMR (CDCl$_3$) δ 1.46 (s, 9H), 4.99 (s, 1H), 6.74 (d, 1H, J=8.1 Hz), 7.28 (d, 1H, J=2.3 Hz), 7.31 (d, 1H, J=2.4 Hz), 7.41 (t, 2H, J=7.2 Hz), 7.50 (d, 1H, J=2.2 Hz), 7.53 (s, 1H), 7.56 (d, 1H, J=1.4 Hz).

(c) 5-bromo-3-(tert-butyl)biphenyl-4-ol 27.00 g (120.0 mmol) of the compound obtained in Example 20(b) and 120 ml of dichloromethane are introduced into a round-bottomed flask. The mixture is cooled to 0° C., 6.4 ml (131.0 mmol) of bromine are added dropwise and the mixture is stirred for ten minutes at 0° C. A saturated sodium thiosulphate solution is added, extraction is carried out with dichloromethane and the organic phase is separated by settling, washed with water to neutral pH, dried over magnesium sulphate and evaporated. 32.00 g (88%) of the expected product are collected in the form of a yellow oil.

$^1$H NMR (CDCl$_3$) δ 1.45 (s, 9H), 5.83 (s, 1H), 7.28 to 7.34 (m, 1H), 7.40 (d, 2H, J=7.6 Hz), 7.44 (d, 1H, J=1.9 Hz), 7.49 to 7.53 (d, 2H, J=8.6 Hz), 7.57 (d, 1H, J=2.2 Hz).

(d) 5-bromo-3-tert-butyl-4-(methoxymethoxy)biphenyl

In a way analogous to Example 13(a), by reaction of 7.30 g (24.0 mmol) of the compound obtained in Example 20(c) with 2.0 ml (26.4 mmol) of chloromethyl methyl ether, 8.00 g (100%) of the expected compound are obtained in the form of an orange oil.

$^1$H NMR (CDCl$_3$) δ 1.48 (s, 9H), 3.71 (s, 3H), 5.16 (s, 2H), 7.34 to 7.46 (m, 3H), 7.51 to 7.54 (m, 3H), 7.64 (d, 1H, J=2.0 Hz).

(e) 5-tert-butyl-4-(methoxymethoxy)biphenyl-3-carbaldehyde

In a way analogous to Example 3(a), from 7.80 g (23.0 mmol) of the compound obtained in Example 20(d), 4.31 g (63%) of the expected compound are obtained in the form of a yellow solid with a melting point of 92–94° C.

$^1$H NMR (CDCl$_3$) δ 1.49 (s, 9H), 3.66 (s, 3H), 5.09 (s, 2H), 7.38 (d, 1H, J=8.5 Hz), 7.44 (t, 2H, J=7.0 Hz), 7.58 (d, 2H, J=8.5 Hz), 7.82 (d, 1H, J=2.5 Hz), 7.94 (d, 1H, J=2.4 Hz), 10.27 (s, 1H).

(f) 1-(5-tert-butyl-4-(methoxymethoxy)biphenyl-3-yl)-3-(trimethylsilanyl)prop-2-yn-1-ol In a way analogous to Example 7(g), from 4.30 g (14.4 mmol) of the compound obtained in Example 20(e), 4.00 g (70%) of the expected compound are obtained in the form of a yellow solid with a melting point of 90–91° C.

$^1$H NMR (CDCl$_3$) δ 0.21 (s, 9H), 1.45 (s, 9H), 3.74 (s, 3H), 3.87 (d, 1H, J=5.5 Hz), 4.96 (d, 1H, J=6.2 Hz), 5.15 (d, 1H, J=6.2 Hz), 5.84 (d, 1H, J=5.5 Hz), 7.36 (d, 1H, J=7.1 Hz), 7.46 (t, 2H, J=7.0 Hz), 7.59 to 7.62 (m, 3H), 7.96 (d, 1H, J=2.4 Hz).

(g) 1-(5-tert-butyl-4-(methoxymethoxy)biphenyl-3-yl)-prop-2-yn1-ol

In a way analogous to Example 7(h), from 4.00 g (10.1 mmol) of the compound obtained in Example 20(f), 3.27 g (100%) of the expected compound are obtained in the form of an orange oil.

$^1$H NMR (CDCl$_3$) δ 1.37 (s, 9H), 2.55 (d, 1H, J=2.3 Hz), 3.66 (s, 3H), 4.89 (d, 1H, J=6.3 Hz), 5.07 (d, 1H, J=6.2 Hz), 5.79 (d, 1H, J=2.1 Hz), 7.24 to 7.46 (m, 3H), 7.50 to 7.54 (m, 3H), 7.85 (d, 1H, J=2.3 Hz).

(h) Ethyl 4-[3-(5-tert-butyl-4-(methoxymethoxy)biphenyl-3-yl)-3-hydroxyprop-1-ynyl]benzoate In a way analogous to Example 3(c), by reaction of 3.20 g (9.9 mmol) of the compound obtained in Example 20(g) with 3.00 g (10.8 mmol) of ethyl 4-iodobenzoate, 3.00 g (65%) of ethyl 4-[3-(5-tert-butyl-4-(3-hydroxyprop-1-ynyl] benzoate are obtained in the form of a brown oil.

$^1$H NMR (CDCl$_3$) δ 1.39 (t, 3H, J=7.1 Hz), 1.46 (s, 9H)), 3.76 (s, 3H), 3.99 (d, 1H, J=5.5 Hz), 4.37 (q, 2H, J=7.2 Hz), 4.99 (d, 1H, J=6.3 Hz), 5.17 (d, 1H, J=6.3 Hz), 7.35 (d, 1H, J=7.1 Hz), 7.44 (t, 1H, J=7.5 Hz), 7.53 (d, 2H, J=8.3 Hz), 7.57 to 7.61 (m, 4H), 7.96 (s, 1H), 7.98 (d, 2H, J=8.1 Hz).

EXAMPLE 21

4-[3-(5-tert-Butyl-4-(methoxymethoxy)biphenyl-3-yl)-3-hydroxyprop-1-ynyl]benzoic Acid In a way analogous to Example 2, from 1.50 g (3.2 mmol) of the compound obtained in Example 20(h), 970 mg (70%) of 4-[3-(5-tert-butyl-4-(methoxymethoxy)-biphenyl-3-yl)-3-hydroxyprop-1-ynyl]benzoic acid are obtained in the form of a beige powder with a melting point of 162–164° C.

$^1$H NMR (d$_6$-DMSO) δ 1.44 (s, 9H), 3.63 (s, 3H), 5.11 (d, 1H, J=5.2 Hz), 5.18 (d, 1H, J=5.2 Hz), 5.94 (d, 1H, J=6.2 Hz), 6.30 (d, 1H, J=6.3 Hz), 7.37 (d, 1H, J=7.3 Hz), 7.46 (d, 2H, J=7.6 Hz), 7.52 to 7.55 (m, 3H), 7.62 (d, 2H, J=7.5 Hz), 7.85 (d, 1H, J=2.0 Hz), 7.91 (d, 2H, J=8.1 Hz), 13.14 (s, 1H).

EXAMPLE 22

Ethyl 4-[3-(5-tert-Butyl-4-methoxybiphenyl-3-yl)-3-hydroxyprop-1-ynyl]benzoate (a) 5-bromo-3-tert-butyl-4-methoxybiphenyl In a way analogous to Example 13(a), by reaction of 4.00 g (13.0 mmol) of the compound obtained in Example 20(c) with 890 μl (14.3 mmol) of methyl iodide, 4.09 g (98%) of the expected compound are obtained in the form of a yellow oil.

$^1$H NMR (CDCl$_3$) δ 1.44 (s, 9H), 3.97 (s, 3H), 7.34 to 7.54 (m, 5H), 7.47 (d, 1H, J=2.1 Hz), 7.65 (d, 1H, J=2.0 Hz).

(b) 5-tert-butyl-4-methoxybiphenyl-3-carbaldehyde

In a way analogous to Example 3(a), from 3.80 g (12.0 mmol) of the compound obtained in Example 22(a), 2.29 g (71%) of the expected compound are obtained in the form of a yellow solid with a melting point of 45° C.

$^1$H NMR (CDCl$_3$) δ 1.47 (s, 9H), 3.99 (s, 3H), 7.32 to 7.59 (m, 5H), 7.79 (d, 1H, J=2.1 Hz), 7.93 (d, 1H, J=2.2 Hz), 10.40 (s, 1H).

(c) 1-(5-tert-butyl-4-methoxybiphenyl-3-yl)-3-trimethylsilanyl)prop-2-yn-1-ol

In a way analogous to Example 7(g), from 2.29 g (8.5 mmol) of the compound obtained in Example 22(b), 2.00 g (64%) of the expected compound are obtained in the form of a yellow solid with a melting point of 94–96° C.

$^1$H NMR (CDCl$_3$) δ 0.21 (s, 9H), 1.46 (s, 3H), 2.56 (d, 1H, J=5.3 Hz), 3.96 (s, 3H), 5.86 (d, 1H, J=5.2 Hz), 7.37 (d, 1H, J=7.1 Hz), 7.46 (t, 2H, J=7.0 Hz), 7.56 (d, 1H, J=2.4 Hz), 7.60 (d, 2H, J=7.6 Hz), 7.83 (d, 1H, J=2.3 Hz).

(d) 1-(5-tert-butyl-4-methoxybiphenyl-3-yl)prop-2-yn-1-ol

In a way analogous to Example 7(h), from 2.00 g (5.5 mmol) of the compound obtained in Example 22(c), 1.52 g (95%) of the expected compound are obtained in the form of a yellow oil.

$^1$H NMR (CDCl$_3$) δ 1.38 (s, 9H), 2.57 (d, 1H, J=2.3 Hz), 3.87 (s, 3H), 5.79 (br s, 1H), 7.24 to 7.40 (m, 6H), 7.74 (d, 1H, J=2.3 Hz).

(e) Ethyl 4-[3-(5-tert-butyl-4-methoxybiphenyl-3-yl)-3-hydroxyprop-1-ynyl]benzoate In a way analogous to Example 3(c), by reaction of 1.50 g (5.1 mmol) of the compound obtained in Example 22(d) with 1.55 g (5.6 mmol) of ethyl 4-iodobenzoate, 1.88 g (83%) of ethyl 4-[3-(5-tert-butyl-4-methoxybiphenyl-3-yl)-3-hydroxyprop-1-ynyl]benzoate are obtained in the form of a reddish oil.

$^1$H NMR (CDCl$_3$) δ 1.39 (t, 3H, J=7.2 Hz), 1.46 (s, 9H), 2.67 (d, 1H, J=5.3 Hz), 3.99 (s, 3H), 4.37 (q, 2H, J=7.1 Hz), 6.10 (d, 1H, J=5.2 Hz), 7.34 to 7.60 (m, 8H), 7.85 (d, 1H, J=2.3 Hz), 7.98 (d, 2H, J=8.4 Hz)

EXAMPLE 23

4-[3-(5-tert-Butyl-4-methoxybiphenyl-3-yl)-3-hydroxyprop-1-ynyl]benzoic Acid

In a way analogous to Example 2, from 1.88 g (4.2 mmol) of the compound obtained in Example 22(e), 1.25 g (72%) of 4-[3-(5-tert-butyl-4-methoxybiphenyl-3-yl)-3-hydroxyprop-1-ynyl]benzoic acid are obtained in the form of a beige powder with a melting point of 165–167° C.

$^1$H NMR (d$_6$-DMSO) δ 1.42 (s, 9H), 3.90 (s, 3H), 5.88 (br s, 1H), 6.32 (br s, 1H), 7.37 (d, 1H, J=7.2 Hz), 7.45 to 7.51 (m, 3H), 7.54 (d, 2H, J=8.3 Hz), 7.62 (d, 2H, J=7.2 Hz), 7.83 (d, 1H, J=2.3 Hz), 7.91 (d, 2H, J=8.3 Hz).

EXAMPLE 24

Ethyl 4-[3-(3,5-di-tert-butyl-2-methoxyphenyl)-3-methoxyprop-1-ynyl]benzoate (a) 1(3,5-di-tert-butyl-2-methoxyphenyl)-1-methoxyprop-2-yne In a way analogous to Example 13(a), by reaction of 1.30 g (5.0 mmol) of 1-(3,5-di-tert-butyl-2-hydroxyphenyl)prop-2-yn-1-ol obtained in Example 13(d) with 340 µl (5.5 mmol) of methyl iodide, 600 mg (41%) of the expected compound are obtained in the form of a yellow solid with a melting point of 68–70° C.

$^1$H NMR (CDCl$_3$) δ 1.32 (s, 9H), 1.39 (s, 9H), 2.58 (d, 1H, J=2.2 Hz), 3.47 (s, 3H), 3.82 (s, 3H), 5.34 (d, 1H, J=2.2 Hz), 7.34 (d, 1H, J=2.5 Hz), 7.54 (d, 1H, J=2.5 Hz).

(b) Ethyl 4-[3-(3,5-di-tert-butyl-2-methoxyphenyl)-3-methoxyprop-1-ynyl]benzoate In a way analogous to Example 3(c), by reaction of 220 mg (0.8 mmol) of the compound obtained in Example 24(a) with 220 mg (0.8 mmol) of ethyl 4-iodobenzoate, 260 mg (74%) of ethyl 4-[3-(3,5-di-tert-butyl-2-methoxyphenyl)-3-methoxyprop-1-ynyl]benzoate are obtained in the form of an orange oil.

$^1$H NMR (CDCl$_3$) δ 1.33 (s, 9H), 1.38 (t, 3H, J=7.1 Hz), 1.41 (s, 9H), 3.53 (s, 3H), 3.88 (s, 3H), 4.37 (q, 2H, J=7.1 Hz), 5.57 (s, 1H), 7.36 (d, 1H, J=2.5 Hz), 7.51 (d, 1H, J=8.4 Hz), 7.62 (d, 1H, J=2.5 Hz), 7.99 (d, 1H, J=8.4 Hz).

EXAMPLE 25

4-[3-(3,5-Di-tert-butyl-2-methoxyphenyl)-3-methoxyprop-1-ynyl]benzoic Acid

In a way analogous to Example 2, from 260 mg (0.6 mmol) of the compound obtained in Example 24(b), 180 mg (73%) of 4-[3-(3,5-di-tert-butyl-2-methoxyphenyl)-3-methoxyprop-1-ynyl]benzoic acid are obtained in the form of a beige powder with a melting point of 162–164° C.

$^1$H NMR (CDCl$_3$) δ 1.33 (s, 9H), 1.41 (s, 9H), 3.54 (s, 3H), 3.88 (s, 3H), 5.58 (s, 1H), 7.36 (d, 1H, J=2.5 Hz), 7.55 (d, 1H, J=8.3 Hz), 7.62 (d, 1H, J=2.5 Hz), 8.06 (d, 1H, J=8.4 Hz).

EXAMPLE 26

Methyl 4-[3-(4,4-dimethylthiochroman-8-yl)prop-1-ynyl]benzoate

In a way analogous to Example 3(c), by reaction of 4.00 g (18.5 mmol) of the compound obtained in Example 5(c) with 3.88 g (14.8 mmol) of methyl 4-iodobenzoate, 1.66 g (25%) of methyl 4-[3-(4,4-dimethylthiochroman-8-yl)prop-1-ynyl]benzoate are obtained in the form of a yellow powder with a melting point of 92° C.

$^1$H NMR (CDCl$_3$) δ 1.35 (s, 6H), 1.96 (t, 2H, J=6.0 Hz), 3.05 (t, 2H, J=6.2 Hz), 3.77 (s, 2H), 3.91 (s, 3H), 7.07 (t, 1H, J=7.7 Hz), 7.33 (d, 1H, J=7.0 Hz), 7.42 (d, 1H, J=7.3 Hz), 7.51 (d, 2H, J=8.4 Hz), 7.97 (d, 2H, J=8.4 Hz).

EXAMPLE 27

Ethyl 6-[3-(4,4-dimethylthiochroman-8-yl)prop-1-ynyl]nicotinate

In a way analogous to Example 3(c), by reaction of 1.00 g (4.6 mmol) of the compound obtained in Example 5(c) with 1.41 g (5.1 mmol) of ethyl 6-iodopyridine-3-carboxylate, 50 mg (3%) of ethyl 6-[3-(4,4-dimethylthiochroman-8-yl)prop-1-ynyl]nicotinate are obtained in the form of a yellow oil.

$^1$H NMR (CDCl$_3$) δ 1.35 (s, 6H), 1.41 (t, 3H, J=7.2 Hz), 1.97 (t, 2H, J=6.0 Hz), 3.06 (t, 2H, J=6.1 Hz), 3.82 (s, 2H), 4.4; (q, 2H, J=7.1 Hz), 7.06 (t, 1H, J=7.7 Hz), 7.34 (d, 1H, J=7.9 Hz), 7.42 (d, 1H, J=7.4 Hz), 7.51 (d, 1H, J=8.2 Hz), 8.23 (dd, 1H, J=8.1/2.1 Hz), 9.16 (d, 1H, J=1.8 Hz).

EXAMPLE 28

4-[3-(4,4-Diethylthiochroman-8-yl)prop-1-ynyl]benzaldehyde

In a way analogous to Example 3(c), by reaction of 2.00 g (9.3 mmol) of the compound obtained in Example 5(c) with 1.88 g (10.2 mmol) of 4-bromobenzaldeyde, 90 mg (5%) of 4-[3-(4,4-dimethylthiochroman-8-yl)prop-1-ynyl] benzaldehyde are obtained in the form of a yellow powder with a melting point of 55–63° C.

$^1$H NMR (CDCl$_3$) δ 1.34 (s, 6H), 1.95 (t, 2H, J=6.1 Hz), 3.05 (t, 2H, J=6.2 Hz), 7.00 (t, 1H, J=8.6 Hz), 7.17 (dd, 1H, J=7.5/1.2 Hz), 7.29 (dd, 1H, J=7.1/1.3 Hz), 7.58 (d, 2H, J=8.2 Hz), 7.80 (d, 2H, J=8.2 Hz), 9.94 (s, 1H).

EXAMPLE 29

4-[3-(4,4-Dimethylthiochroman-8-yl)prop-1-ynyl]phenol

In a way analogous to Example 3(c), by reaction of 1.00 g (4.6 mmol) of the compound obtained in Example 5(c) with 880 mg (5.1 mmol) of 4-bromophenol, 286 mg (20%) of 4-[3-(4,4-dimethylthiochroman-8-yl)-prop-1-ynyl]phenol are obtained in the form of a yellow powder with a melting point of 95° C.

$^1$H NMR (CDCl$_3$) δ 1.33 (s, 6H), 1.94 (t, 2H, J=6.0 Hz), 3.03 (t, 2H, J=6.1 Hz), 3.72 (s, 2H), 6.75 (d, 2H, J=8.7 Hz), 7.07 (t, 1H, J=7.7 Hz), 7.27 to 7.34 (m, 3H), 7.46 (d, 1H, J=7.4 Hz).

EXAMPLE 30

Ethyl 4-[3-(5-tert-butyl-4-hydroxybiphenyl-3-yl)-3-hydroxyprop-1-ynyl]benzoate 1.44 g (3.0 mmol) of the compound obtained in Example 20(h) and 15 ml of ethanol are introduced into a 100 ml three-necked flask under a stream of nitrogen. 830 µl (15.0 mmol) of concentrated sulphuric acid are added dropwise. The reaction mixture is stirred for three hours at room temperature, water is then added, extraction is carried out with ethyl ether, the organic phase is washed with water to neutral pH, dried over magnesium sulphate and filtered, and the solvents are evaporated. 1.25 g (100%) of ethyl 4-[3-(5-tert-butyl-4-hydroxybiphenyl-3-yl)-3-hydroxyprop-1-ynyl]benzoate are collected in the form of a reddish oil.

$^1$H NMR (CDCl$_3$) δ 1.43 (t, 3H, J=7.2 Hz), 1.48 (s, 9H), 4.38 (q, 2H, J=7.2 Hz), 5.69 (s, 1H), 7.31 (d, 1H, J=7.1 Hz), 7.38 to 7.44 (m, 3H), 7.52 to 7.56 (m, 5H), 7.97 (s, 1H), 8.00 (d, 2H, J=8.4 Hz).

EXAMPLE 31

4-[3-(5-tert-Butyl-4-methoxybiphenyl-3-yl)prop-1-ynyl]benzoic Acid

In a way analogous to Example 9, from 700 mg (1.7 mmol) of the compound obtained in Example 23, 508 mg (75%) of 4-[3-(5-tert-butyl-4-methoxybiphenyl-3-yl)prop-1-ynyl]benzoic acid are obtained in the form of a white powder with a melting point of 229–231° C.

$^1$H NMR (CDCl$_3$) δ 1.45 (s, 9H), 3.89 (s, 3H), 3.94 (s, 2H), 7.34 (d, 1H, J=7.1 Hz), 7.40 to 7.49 (m, 5H), 7.56 to 7.60 (m, 2H), 7.66 (d, 1H, J=2.2 Hz), 7.98 (d, 2H, J=8.3 Hz).

Examples of Pharmaceutical and Cosmetic Compositions

Various pharmaceutical and cosmetic formulations based on the active compounds according to the invention have been illustrated in the following examples.

A—Oral Route

| (a) 0.2 g tablet | |
|---|---|
| Compound prepared in Example 2 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

The compound according to Example 2 can advantageously be replaced by the same amount of one of the compounds according to Examples 4, 6, 11, 12, 21, 25 or 31.

| (b) Oral suspension in 5 ml phials | |
|---|---|
| Compound prepared in Example 4 | 0.001 g |
| Glycerol | 0.500 g |
| 70% Sorbitol | 0.500 g |
| Sodium saccharinate | 0.010 g |
| Methyl p-hydroxybenzoate | 0.040 g |
| Flavouring q.s. | |
| Purified water q.s. for | 5 ml |

The compound according to Example 4 can advantageously be replaced by the same amount of one of the compounds according to Examples 8, 12, 18 and 19.

| (c) 0.8 g tablet | |
|---|---|
| Compound of Example 6 | 0.500 g |
| Pregelatinized starch | 0.100 g |
| Microcrystalline cellulose | 0.115 g |

-continued

| (c) 0.8 g tablet | |
|---|---|
| Lactose | 0.075 g |
| Magnesium stearate | 0.010 g |

| (d) Oral suspension in 10 ml phials | |
|---|---|
| Compound of Example 6 | 0.200 g |
| Glycerol | 1.000 g |
| 70% Sorbitol | 1.000 g |
| Sodium saccharinate | 0.010 g |
| Methyl p-hydroxybenzoate | 0.080 g |
| Flavouring q.s. | |
| Purified water q.s. for | 10 ml |

The compound according to Example 6 can advantageously be replaced by the same amount of one of the compounds according to Examples 11, 12, 14, 23 or 25.

B—Topical Route

| (a) Ointment | |
|---|---|
| Compound of Example 4 | 0.020 g |
| Isopropyl myristate | 81.700 g |
| Fluid paraffin oil | 9.100 g |
| Silica ("Aerosil 200", sold by Degussa) | 9.180 g |

| (b) Ointment | |
|---|---|
| Compound of Example 1 | 0.300 g |
| White petroleum jelly, pharmaceutical grade | 100 g |

In this example, the compound of Example 1 can advantageously be replaced by the same amount of a compound according to Examples 28 and 29.

| (c) Non-ionic water-in-oil cream | |
|---|---|
| Compound of Example 2 | 0.100 g |
| Mixture of emulsive lanolin alcohols, of waxes and of oils ("Anhydrous eucerin", sold by BDF) | 39.900 g |
| Methyl p-hydroxybenzoate | 0.075 g |
| Propyl p-hydroxybenzoate | 0.075 g |
| Sterile demineralized water q.s. for | 100 g |

| (d) Lotion | |
|---|---|
| Compound of Example 4 | 0.100 g |
| Polyethylene glycol (PEG 400) | 69.900 g |
| 95% Ethanol | 30.000 g |

In the above examples (c) and (d), the compound according to Example 4 can advantageously be replaced by the same amount of one of the compounds according to Examples 6, 9, 11, 14, 21, 23 and 31.

| (e) Hydrophobic ointment | |
|---|---|
| Compound of Example 2 | 0.300 g |
| Isopropyl myristate | 36.400 g |
| Silicone oil ("Rhodorsil 47V300", sold by Rhône-Poulenc) | 36.400 g |
| Beeswax | 13.600 g |
| Silicone oil ("Abil 300.000 cst", sold by Goldschmidt) | 100 g |

| (f) Non-ionic oil-in-water cream | |
|---|---|
| Compound of Example 5 | 1.000 g |
| Cetyl alcohol | 4.000 g |
| Glycerol monostearate | 2.500 g |
| PEG 50 stearate | 2.500 g |
| Karite butter | 9.200 g |
| Propylene glycol | 2.000 g |
| Methyl p-hydroxybenzoate | 0.075 g |
| Propyl p-hydroxybenzoate | 0.075 g |
| Sterile demineralized water q.s. for | 100 g |

In this example, the compound according to Example 5 can advantageously be replaced by the same amount of one of the compounds according to Examples 7, 10, 13, 15, 17, 20 or 22.

What is claimed is:

1. Biaromatic compounds connected by a propynylene or ailenylene bond, corresponding to the following formula (I):

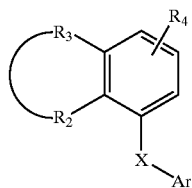

(I)

in which:

Ar represents a radical

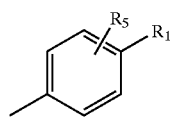

(a)

$R_1$ represents —$CH_3$, —$CH_2$—O—$R_6$, —$OR_6$ or —$COR_7$, $R_2$ and $R_3$, taken together, form a 5- or 6-membered ring interrupted by an oxygen or sulphur atom, said ring being optionally substituted by at least one methyl $R_4$ represents H, halogen, linear or branched $C_1$–$C_{20}$ alkyl, —$OR_8$, a polyether radical or aryl, $R_5$ represents H, a halogen, linear or branched $C_1$–$C_{20}$ alkyl or an —$OR_8$ radical, $R_6$ represents H, lower alkyl or a —$COR_9$ radical, $R_7$ represents H, lower alkyl,

or —$OR_{10}$, $R_8$ represents H, lower alkyl or —$COR_9$, $R_9$ represents lower alkyl, $R_{10}$ represents H, $C_1$–$C_{20}$ alkyl, which can be linear or branched, alkenyl, mono- or polyhydroxyalkyl, optionally substituted aryl or aralkyl, or a sugar residue, r' and r" represent H, lower alkyl, mono- or polyhydroxyalkyl, optionally substituted aryl, or an amino acid or sugar residue or, taken together with the nitrogen atom, form a heterocycle, X represents a divalent radical, which, from right to left or vice versa, has the formula:

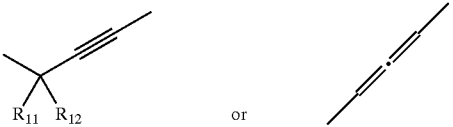

$R_{11}$ and $R_{12}$ are hydrogen, and the salts of the compounds of formula (I), when $R_1$ represents a carboxylic acid functional group, and the optical and geometrical isomers of the compounds of formula (I).

2. Compounds according to claim 1, wherein they are provided in the form of a salt of an alkali metal or alkaline earth metal or alternatively of zinc or of an organic amine.

3. Compounds according to claim 1, wherein the lower alkyl radical is selected from the group consisting of the methyl, ethyl, isopropyl, butyl, tertbutyl and hexyl radicals.

4. Compounds according to claim 1, wherein the $C_1$–$C_{20}$ alkyl radical, which can be linear or branched, is selected from the group consisting of the methyl, ethyl, propyl, isopropyl, hexyl, heptyl, 2-ethylhexyl, octyl, nonyl, dodecyl, hexadecyl and octadecyl radicals.

5. Compounds according to claim 1, wherein the mono-hydroxyalkyl radical is selected from the group consisting of the 2-hydroxyethyl, 2-hydroxypropyl and 3-hydroxypropyl radicals.

6. Compounds according to claim 1, wherein the poly-hydroxyalkyl radical is selected from the group consisting of the 2,3-dihydroxypropyl, 2,3,4-trihvdroxybutyl or 2,3,4,5-tetrahydroxypentyl radicals and the pentaerythritol residue.

7. Compounds according to claim 1, wherein the aryl radical is a phenyl radical optionally substituted by at least one halogen atom, one hydroxyl, one nitro functional group, one lower alkyl, one $CF_3$ radical, one amino radical optionally protected by an acetyl functional group or optionally substituted by one or two lower alkyl(s), one alkoxy radical or one polyether radical.

8. Compounds according to claim 1, wherein the aralkyl radical is selected from the group consisting of benzyl and phenethyl radical optionally substituted by at least one halogen atom, one hydroxyl or one nitro functional group.

9. Compounds according to claim 1, wherein the alkenyl radical is selected from the group consisting of the radicals comprising from 2 to 5 carbon atoms and exhibiting one or two ethylenic unsaturation(s).

10. Compounds according to claim 1, wherein the sugar residue is selected from the group consisting of the glucose, galactose, man-nose and glucuronic acid residues.

11. Compounds according to claim 1, wherein the amino acid residue is selected from the group consisting of the residues deriving from lysine, glycine and aspartic acid.

12. Compounds according to claim 1, wherein the heterocyclic radical is selected from the group consisting of an piperidino radical morpholino radical, pyrrolidino radical and piperazino radical optionally substituted at the 4-position by a $C_1$–$C_6$ alkyl or a mono- or polyhydroxyalkyl.

13. Compounds according to claim 1, wherein the halogen atom is selected from the group consisting of fluorine, chlorine and bromine.

14. A compound selected from the group consisting of:
Methyl 2-hydroxy-4-[3-(4,4-dimethylchroman-8-yl)prop-1-ynyl]benzoate,
2-Hydroxy-4-[3-(4,4-dimethylchroman-8-yl)prop-1-ynyl]benzoic acid,
Methyl 2-hydroxy-4-[3-hydroxy-3-(4,4-dimethylchroman-8-yl)prop-1-ynyl]benzoate,
2-Hydroxy-4-[3-hydroxy-3-(4,4-dimethiochroman-8-yl)prop-1-ynyl]benzoic acid,
Methyl 2-hydroxy-4-[3-(4.4-dimethylthiochroman-8-yl)prop-1-ynyl]benzoate,
2-Hydroxy-4-[3-(4,4-dimethylthiochroman-8-yl)prop-1-ynyl]benzoic acid,
Ethyl 4-[3-(4,4-dimethylthiochroman-5-yl)-3-hydroxyprop-1-ynyl]benzoate,
4-[3-(4,4-Dimethylthiochroman-5-yl)-3-hydroxyprop-1-ynyl]benzoic acid,
4-[3-(4,4-Dimethylthiochroman-5-yl)prop-1-ynyl]benzoic acid,
Methyl 4-[3-(4,4-dimethylthiochroman-8-yl)prop-1-ynyl]benzoate,
4-[3-(4,4-Dimethylthiochroman-8-yl)prop-1-ynyl]benzaldehyde,
4-[3-(4,4-Dimethylthiochroman-8-yl)prop-1-ynyl]phenol,
4-[3-(4,4-Dimethylthiochroman-8-yl)prop-1-ynyl]benzoic acid,
Methyl 2-hydroxy-4-[3-hydroxy-3-(4,4-dimethylchroman-8-yl)prop-1-ynyl]benzoate,
2-Hydroxy-4-[3-hydroxy-3-(4,4-dimethylchroman-8-yl)prop-1-ynyl]benzoic acid,
2-Hydroxy-4-[3-(4,4-dimethylthiochroman-8-yl) prop-1-ynyl]benzoic acid,
4-[3-(4.4-Dimethylthiochroman-8-yl)prop-1-ynyl]benzamide,
N-Ethyl-4-[3-(4,4-dimethylthiochroman-8-yl)prop-1-ynyl]benzamide,
N-(4-Hydroxyphenyl)-4-[3-(4,4-dimethylthiochroman-8-yl)prop-1-ynyl]benzamide,
4-[3-(4,4-Dimethylthiochroman-8-yl)prop-1-ynyl]benzoic acid morpholide,
4-[3-(4,4-Dimethylthiochroman-8-yl)prop-2-ynyl]benzoic acid,
4-[3-(4,4-Dimethyl-6-phenylthiochroman-8-yl)prop-1-ynyl]benzoic acid,
4-[3-(4,4-Dimethyl-6-phenylchroman-8-yl)prop-1-ynyl]benzoic acid,
4-[3-(4,4-Dimethyl-6-phenylthiochroman-8-yl)prop-2-ynyl]benzoic acid, and
4-[3-(4,4-Dimethyl-6-(p-tolyl)thiochroman-8-yl)prop-1-ynyl]benzoic acid.

15. A pharmaceutical composition, comprising in a pharmaceutically acceptable vehicle, at least one compound as defined according to claim 1.

16. The composition according to claim 15, wherein the concentration of at least one compound is present in an amount of 0.001% and 5% by weight with respect to the total weight of the composition.

17. A cosmetic composition comprising in a cosmetically acceptable vehicle, at least one compound according to claim 1.

18. The composition according to claim 17, wherein the concentration of said compound is present in an amount of between 0.001 and 3% by weight with respect to the total weight of the composition.

19. A compound selected from the group consisting of
Methyl 2-hydroxy-4-[3-(4,4-dimethylchroman-8-yl)prop-1-ynyl]benzoate,
2-Hydroxy-4-[3-(4,4-dimethylchroman-8-yl)prop-1-ynyl]benzoic acid,
Methyl 2-hydroxy-4-[3-(4.4-dimethylthiochroman-8-yl)prop-1-ynyl]benzoate,
2-Hydroxy-4-[3-(4,4-dimethylthiochroman-8-yl)prop-1-ynyl]benzoic acid,
4-[3-(4,4-Dimethylthiochroman-5-yl)prop-1-ynyl]benzoic acid,
Methyl 4-[3-(4,4-dimethylthiochroman-8-yl)prop-1-ynyl]benzoate,
4-[3-(4,4-Dimethylthiochroman-8-yl)prop-1-ynyl]benzaldehyde, 4-[3-(4,4-Dimethylthiochroman-8-yl)prop-1-ynyl]phenol,
Methyl 2-hydroxy-4-[3-hydroxy-3-(4,4-dimethylchroman-8-yl)prop-1-yny1]benzoate,
2-Hydroxy-4-[3-hydroxy-3-(4,4-dimethylchroman-8-yl)prop-1-ynyl]benzoic acid, and
Ethyl 4-[3-(4,4-dimethylthiochroman-5-yl)-3-hydroxyprop-1-ynyl]benzoate.

20. A compound of the following formula 2-Hydroxy-4-[3-(4,4-dimethylchroman-8-yl)prop-1-ynyl]benzoic acid.

21. A pharmaceutical composition, comprising in a pharmaceutically acceptable vehicle, at least one compound as defined according to any one of claims 19–20.

22. The composition according to claim 21, wherein the concentration of at least one compound is present in an amount of 0.001% and 5% by weight with respect to the total weight of the composition.

23. A cosmetic composition comprising in a cosmetically acceptable vehicle, at least one compound according to any one of claims 19–20.

24. The composition according to claim 23, wherein the concentration of said compound is present in an amount of between 0.001 and 3% by weight with respect to the total weight of the composition.

25. A compound according to claim 1 wherein Ar represents a radical

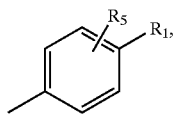

X represents a divalent radical, which, from right to left or vice versa, has the formula:

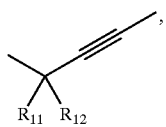

and
$R_{11}$ and $R_{12}$ are hydrogen.

26. A pharmaceutical composition, comprising in a pharmaceutically acceptable vehicle, at least one compound as defined according to claim 25.

27. The composition according to claim 26 wherein the concentration of at least one compound is present in an amount of 0.001% and 5% by weight with respect to the total weight of the composition.

28. A cosmetic composition comprising in a cosmetically acceptable vehicle, at least one compound according to claim 25.

29. The composition according to claim 28, wherein the concentration of said compound is present in an amount of between 0.001 and 3% by weight with respect to the total weight of the composition.

* * * * *